(12) United States Patent
O'Neill et al.

(10) Patent No.: US 11,352,439 B2
(45) Date of Patent: Jun. 7, 2022

(54) MACROPHAGE CAR (MOTO-CAR) IN IMMUNOTHERAPY

(71) Applicants: Kim Leslie O'Neill, Provo, UT (US); Scott Weber, Lindon, UT (US)

(72) Inventors: Kim Leslie O'Neill, Provo, UT (US); Scott Weber, Lindon, UT (US)

(*) Notice: Subject to any disclaimer, the term of this patent is extended or adjusted under 35 U.S.C. 154(b) by 0 days.

(21) Appl. No.: 15/358,395

(22) Filed: Nov. 22, 2016

(65) Prior Publication Data
US 2017/0166657 A1 Jun. 15, 2017

Related U.S. Application Data

(63) Continuation of application No. PCT/IB2016/056140, filed on Oct. 13, 2016, and a continuation-in-part of application No. 15/236,421, filed on Aug. 13, 2016, now abandoned.

(60) Provisional application No. 62/240,528, filed on Oct. 13, 2015, provisional application No. 62/204,935, filed on Aug. 13, 2015.

(51) Int. Cl.
| | |
|---|---|
| C07K 16/40 | (2006.01) |
| C07K 14/705 | (2006.01) |
| C07K 14/57 | (2006.01) |
| C07K 16/28 | (2006.01) |
| C07K 16/18 | (2006.01) |
| C12N 5/0786 | (2010.01) |
| A61K 35/15 | (2015.01) |
| C07K 16/30 | (2006.01) |
| A61K 38/00 | (2006.01) |
| A61K 39/00 | (2006.01) |

(52) U.S. Cl.
CPC ............ *C07K 16/40* (2013.01); *A61K 35/15* (2013.01); *C07K 14/57* (2013.01); *C07K 14/705* (2013.01); *C07K 14/70503* (2013.01); *C07K 16/18* (2013.01); *C07K 16/2866* (2013.01); *C07K 16/30* (2013.01); *C12N 5/0645* (2013.01); *C12Y 204/02008* (2013.01); *C12Y 207/01021* (2013.01); *A61K 38/00* (2013.01); *A61K 2039/505* (2013.01); *C07K 2317/31* (2013.01); *C07K 2317/622* (2013.01); *C07K 2319/74* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 499,629 A | 6/1893 | Ellis | |
| 906,682 A | 12/1908 | Birkeland | |
| 911,993 A | 2/1909 | Jacobs | |
| 916,381 A | 3/1909 | Webster | |
| 5,359,046 A * | 10/1994 | Capon | C07K 14/7051 435/235.1 |
| 7,837,998 B2 | 11/2010 | Lallatin et al. | |
| 8,906,682 B2 | 12/2014 | June | |
| 8,911,993 B2 | 12/2014 | June | |
| 8,916,381 B1 | 12/2014 | June | |
| 9,393,268 B2 | 7/2016 | Waldman et al. | |
| 9,499,629 B2 | 11/2016 | June | |
| 10,415,017 B2 | 9/2019 | ONeill | |
| 10,434,153 B1 | 10/2019 | ONeill et al. | |
| 2010/0143290 A1 | 6/2010 | Lallatin | |
| 2010/0266495 A1* | 10/2010 | O'Neill | A61K 31/513 424/1.49 |
| 2011/0176996 A1 | 7/2011 | O'neill | |
| 2014/0242701 A1* | 8/2014 | Shiku | C07K 14/7051 435/455 |
| 2016/0145348 A1 | 5/2016 | Stephan | |
| 2018/0244748 A1 | 1/2018 | Gill et al. | |

FOREIGN PATENT DOCUMENTS

| | | | | |
|---|---|---|---|---|
| JP | 2017500869 A | 1/2017 | | |
| WO | 2010065763 A1 | 6/2010 | | |
| WO | 2011082345 A2 | 7/2011 | | |
| WO | 2015063069 A1 | 5/2015 | | |
| WO | WO-2015094106 A1 * | 6/2015 | ........... G01N 33/573 | |
| WO | WO 2016033331 A1 * | 3/2016 | ......... C07K 14/7051 | |
| WO | 2017025944 A2 | 2/2017 | | |
| WO | WO 2017019848 A1 * | 2/2017 | ......... C07K 14/7051 | |
| WO | 2018212770 A1 | 11/2018 | | |
| WO | WO2018212770 A1 | 11/2018 | | |

OTHER PUBLICATIONS

Wang et al (CR:70(12):4840-9, 2010).*
Sinha et al (JI, 174:636-645, 2005).*
Palaga et al (EJI, 38:174-183).*
Bulut et al (JI, 168:1435-1440).*
Levin et al (GT, 19:1041 -1047, 2012).*
Lloyd et al (Protein Engineering, Design & Selection, 22:159-168, 2009).*
Edwards et al (J Mol Biol, 14;334(1):103-118, 2003).*
Celhar et al (II, 28(5):223-232, 2015).*
Carman S.M. Yong et al: "Using Electroporation to Determine Function of a Chimeric Antigen Receptor in T Cell and Macrophage Cell Lines" The Open Gene Therapy Journal, vol. 5 No.1, Aug. 23, 2013, pp. 1-11.
Phillip K Darcy et al. "Manipulating immune cells for adoptive immunotherapy of cancer", Current Opinion in Immunology, vol. 27, Apr. 1, 2014.
Paul S et al: "Targeted macrophage cytotoxicity using a nonreplicative live vector expressing a tumor-specific single-chain variable region fragment" Human Gene Therapy, Maryann Liebert, Inc. Publichers, US, vol. 11, No. 10, Jul. 1, 2000.
Zhang F et al: "A monoclonal antibody specific for human thymidine kinase 1" Hybroidoma, Liebert, New York, NY, US, vo. 20, No. 1 Feb. 1, 2001.
PCT/IB2016/056140 WO2017025944 Search Report Opinion—dated Jan. 23, 2017.

(Continued)

*Primary Examiner* — Brad Duffy
(74) *Attorney, Agent, or Firm* — Patent Law Works, LLP

(57) ABSTRACT

Modified macrophage immune cells are provided for treatment of cancer and other diseases.

12 Claims, 10 Drawing Sheets

(56) References Cited

OTHER PUBLICATIONS

European Patent Office Communication Pursuant to Article 94(3) EPC, Application No. 16801306.8, dated Jan. 30, 2019, 5 pages.
Abken, Hinrich, Driving CARs on the Highway to Solid Cancer: Some Considerations on the Adoptive Therapy with CAR T Cells, Human Gene Therapy, vol. 28, No. 11, 2017, doi:10.1089/hum.2017.115, pp. 1047-1060.
Lo et al., Regression of established renal cell carcinoma in nude mice using lentivirus-transduced human T cells expressing a human anti-CAIX chimeric antigen receptor, Molecular Therapy, Oncolytics, 2014, vol. 1, doi:10.1038/mto.2014.3.
Murphy et al., The prolonged Life-Span of Alveolar Macrophages, Am J Respir Cell Mol Biol, 2008, pp. 380-385, vol. 38.
European Patent Office Communication Pursuant to Article 94(3) EPC, Application No. 16801306.8, dated Feb. 14, 2019, 4 pages.
Appendix A of Feb. 29, 2020, Remarks of Mar. 15, 2018 filing in U.S. Appl. No. 15/161,045, by Daniel J. Morath, Ph.D. 8 pages.
Biglari, et al. (2006) "Human monocytes expressing a CEA-specific chimeric CD64 receptor specifically target CEA-expressing tumour cells in vitro and in vivo", Gene Therapy, 13: 602-10.
CD Creative Diagnostics, Resources, "4-1BB/4-1BBL Signaling Pathway", https://www.creative-diagnostics.com/4-1bb-4-1bbl-signaling-pathway.htm, accessed Dec. 29, 2020, 2 pgs.
European Patent Office Communication Pursuant to Article 94(3) EPC, Application No. 16801306.8, dated Feb. 14, 2020, 4 pages.
Frohlich, Anne, et al. "Comprehensive Analysis of Tumor Necrosis Factor Receptor TNFRSF9 (4-1BB) DNA Methylation with Regard to Molecular and Clinicopathological Features, Immune Infiltrates, and Response Prediction to Immunotherapy in Melanoma." EBioMedicine, vol. 52, 2020, p. 102647.
Gunaydin, et al. (2014) "Mutations in Toll-Like Receptor 3 Are Associated with Elevated Levels of Rotavirus-Specific IgG Antibodies in IgA-Deficient but Not IgA-Sufficient Individuals", Cancer and Vaccine Immunology, 21(3): 298-301 (Year: 2014).
Kochenderfer, et al. (Apr. 2, 2013) "Treating B-cell cancer with T cells expressing anti-CD19 chimeric antigen receptors", Nature Reviews Clinical Oncology, 10: 267-76.
Langstein, Joachim, et al. "CD137 (ILA/4-1BB), a Member of the TNF Receptor Family, Induces Monocyte Activation via Bidirectional Signaling." The Journal of Immunology (1950), vol. 160, No. 5, 1998, pp. 2488-2494.
Macrophages on Immunology website (visited Mar. 16, 2018), http://cellular-immunity.blogspot.com/2007/12/macrophages.html.
Orecchioni, Marco, et al. "Macrophage Polarization: Different Gene Signatures in M1(LPS) vs. Classically and M2 (LPS-) vs Alternatively Activated Macrophages" Frontiers in Immunology, vol. 10, 2019, p. 1084.
PCT International Search Report and Written Opinion, PCT/US2017/033039, dated Jan. 30, 2018, 10 pages.
Rossi, et al. (Dec. 2, 2013) "A new class of bispecific antibodies to redirect T cells for cancer immunotherapy", MAbs, 6(2): 381-91.
Sarlus, et al. (2017) "Micrglia in Alzheimers disease", The Journal of Clinical Investigation, 127(9): 3240-49. (Year: 2017).
Sharp, et al. (2011) "Abstract 897: Thymidine kinase 1, a novel biomarker specific to the plasma membrane of cancerous cell lines", (Proceedings of the 102nd Annual Meeting of the American Association for Cancer Research, Apr. 2-6, Orlando, FL), Cancer Research, 71(8 Suppl), Abstract 897.
Wynn, et al. (2015) "Macrophages in Tissue Repair, Regeneration and Fibrosis", Immunity, 44: 450-462. (Year: 2015).
Japanese Office Action, Notice of Reasons for Rejection, dated Jun. 14, 2021, Application No. 2020-514655, 10 pgs.
Japanese Office Action, Notice of Reasons for Rejection, dated Jan. 31, 2022, Application No. 2020-514655, 8 pgs wiith translation.
Quatromoni, Jon G., et al., "Tumor-Associated Macrophages: Function, Phenotype, and Link to Prognosis in Human Lung Cancer" Am. Journal Transl Res., Oct. 30, 2012, vol. 4 (4): pp. 376-389.

* cited by examiner

MACROPHAGE CAR (MOTO-CAR) IN IMMUNOTHERAPY

CROSS REFERENCE TO RELATED APPLICATIONS

This is a continuation-in-part from U.S. patent application Ser. No. 15/236,421, filed 13 Aug. 2016, which claims priority from U.S. Provisional Patent Applications 62/204,935, filed 13 Aug. 2015, and 62/240,528 filed 13 Oct. 2015, which are hereby incorporated by reference.

This is a continuation from Patent Application filed under the Patent Cooperation Treaty PCT/IB2016/056140, filed 13 Oct. 2016, which claims priority from U.S. patent application Ser. No. 15/236,421, filed 13 Aug. 2016, and from U.S. Provisional Patent Applications 62/204,935, filed 13 Aug. 2015, and 62/240,528 filed 13 Oct. 2015, which are hereby incorporated by reference.

BACKGROUND

Cancer describes of a group of diseases which involve unregulated cell growth and death, genome instability and mutations, tumor-promoting inflammation, induction of angiogenesis, immune system evasion, deregulation of metabolic pathways, immortal cell replication, and metastatic tissue invasion [1]. Cancer is the second leading cause of death in the United States after heart disease [2]. More than 1.6 million new cases of cancer are projected to be diagnosed each year, with more than 580,000 Americans expected to die (about 1600 cancer deaths per day), accounting for nearly 1 in 4 of all American deaths [2,3].

The immune system plays an important role in the development of and progression of cancer. Monocytes, which differentiate into macrophages, display a variety of responses according to varying stimuli and exhibit different functions depending on the microenvironment surrounding them. Macrophages can be pro-inflammatory (M1) or anti-inflammatory (M2). Research studies have shown that infiltration of macrophages into the tumor site can account for greater than 50% of the tumor mass, aid in metastasis by inducing angiogenesis, and signify poor prognosis. Macrophages that migrate to and remain in the tumor site promoting angiogenesis and metastasis are termed tumor associated macrophages (TAMs) and are thought to express an anti-inflammatory M2 phenotype.

Macrophages are cells derived from the myeloid lineage and belong to the innate immune system. They are derived from blood monocytes that migrate into tissue. One of their main functions is to phagocytose microbes and clear cellular debris. They also play an important role in both the initiation and resolution of inflammation [9, 10]. Moreover, macrophages can display different responses, ranging from pro-inflammatory to anti-inflammatory, depending on the type of stimuli they receive from the surrounding microenvironment [11]. Two major macrophage phenotypes have been proposed which correlate with extreme macrophage responses: M1 and M2.

M1 pro-inflammatory macrophages are activated upon contact with certain molecules such as lipopolysaccharide (LPS), IFN-γ, IL-1β, TNF-α, and Toll-like receptor engagement. M1 macrophages constitute a potent arm of the immune system deployed to fight infections. They are capable of either direct (pathogen pattern recognition receptors) or indirect (Fe receptors, complement receptors) recognition of the pathogen. They are also armed in their ability to produce reactive oxygen species (ROS) as means to help killing pathogens. In addition, M1 macrophages secrete pro-inflammatory cytokines and chemokines attracting other types of immune cells and integrating/orchestrating the immune response. M1 activation is induced by IFN-g, TNFα, GM-CSF, LPS and other toll-like receptors (TLR) ligands.

In contrast, M2 anti-inflammatory macrophages, also known as alternatively activated macrophages, are activated by anti-inflammatory molecules such as IL-4, IL-13, and IL-10 [12, 13]. M2 macrophages exhibit immunomodulatory, tissue repair, and angiogenesis properties which allow them to recruit regulatory T cells to sites of inflammation. M2 macrophages do not constitute a uniform population and often are further subdivided into M2a, M2b and M2c categories. The common denominator of all three subpopulations is high IL-10 production accompanied by low production of IL-12. One of their signatures is production of enzyme Arginase-1 that depletes L-arginine thereby suppressing T cell responses and depriving iNOS of its substrate.

The in vivo molecular mechanisms of macrophage polarization are poorly characterized because of the variety of signals macrophages experience in the cellular microenvironment [10, 14]. In recent years, progress has been made in identifying in vivo macrophage polarization under physiological conditions such as ontogenesis, pregnancy, and pathological conditions such as allergies, chronic inflammation, and cancer. It is not known, however, that in vitro macrophage polarization is plastic and macrophages, with the help of cytokines, can be polarized back and forth to either phenotype [15, 16]. Interferon gamma (IFN-γ) and IL-4 are two cytokines that can polarize macrophages to M1 and M2 phenotypes, respectively [15].

The presence of macrophages is crucial for tumor progression and growth, and has implications in determining prognosis [17, 18]. Because macrophages can exhibit both pro-inflammatory and anti-inflammatory properties, it is important to understand their polarization and function in tumor progression and metastasis.

Macrophage Polarization

The tumor microenvironment can affect macrophage polarization. The process of polarization can be diverse and complex because of the hostile environment of IL-10, glucocorticoid hormones, apoptotic cells, and immune complexes that can interfere with innate immune cells function [11, 19]. The mechanisms of polarization are still unclear but it is known they involve transcriptional regulation. For example, macrophages exposed to LPS or IFN-γ will polarize towards an M1 phenotype, whereas macrophages exposed to IL-4 or IL-13 will polarize towards an M2 phenotype. LPS or IFN-γ can interact with Toll-like receptor 4 (TLR4) on the surface of macrophages inducing the Trif and MyD88 pathways, inducing the activation of transcription factors IRF3, AP-1, and NFκB and thus activating TNFs genes, interferon genes, CXCL10, NOS2, IL-12, etc. which are necessary in a pro-inflammatory M1 macrophage response [20]. Similarly, IL-4 and IL-13 bind to IL-4R, activation the Jak/Stat6 pathway, which regulates the expression of CCL17, ARG1, IRF4, IL-10, SOCS3, etc., which are genes associated with an anti-inflammatory response (M2 response).

Additional mechanisms of macrophage polarization include microRNA (miRNA) micromanagement. miRNAs are small non-coding RNA of 22 nucleotides in length that regulate gene expression post-transcriptionally, as they affect the rate of mRNA degradation. Several miRNAs have been shown to be highly expressed in polarized macrophages, especially miRNA-155, miRNA-125, miRNA-378 (M1 polarization), and miRNA let-7c, miRNA-9, miRNA-21, miRNA-146, miRNA147, miRNA-187 (M2 polarization) [21].

Macrophage polarization is a complex process where macrophages behave and elicit different responses depending on microenvironment stimuli. Therefore, macrophage polarization is better represented by a continuum of activation states where M1 and M2 phenotypes are the extremes of the spectrum. In recent years, there has been much controversy on the definition/description of macrophage activation and macrophage polarization. A recent paper published by Murray et al. they describe a set of standards to be considered for the consensus definition/description of macrophage activation, polarization, activators, and markers. This publication was much needed for the definition and characterization of activated/polarized macrophages [22].

M1 Phenotype

M1 pro-inflammatory macrophages or classically activated macrophages are aggressive, highly phagocytic, and produce large amounts of reactive oxygen and nitrogen species, thereby promoting a Th1 response [11]. M1 macrophages secrete high levels of two important inflammatory cytokines, IL-12 and IL-23. IL-12 induces the activation and clonal expansion of Th17 cells, which secrete high amounts of IL-17, which contributes to inflammation [23]. These characteristics allow M1 macrophages to control metastasis, suppress tumor growth, and control microbial infections [24]. Moreover, the infiltration and recruitment of M1 macrophages to tumor sites correlates with a better prognosis and higher overall survival rates in patients with solid tumors [17, 18, 25-28].

Polarization of macrophages to the M1 phenotype is regulated in vitro by inflammatory signals such as IFN-γ, TNF-α, IL-1β and LPS as well as transcription factors and miRNAs [29, 30]. Classically activated macrophages initiate the induction of the STAT1 transcription factor which targets CXCL9, CXCL10 (also known as IP-10), IFN regulatory factor-1, and suppressor of cytokine signaling-1 [31]. Cytokine signaling-1 protein functions downstream of cytokine receptors, and takes part in a negative feedback loop to attenuate cytokine signaling. In the tumor microenvironment, Notch signaling plays an important role in the polarization of M1 macrophages, as it allows transcription factor RBP-J to regulate classical activation.

Macrophages that are deficient in Notch signaling express an M2 phenotype regardless of other extrinsic inducers [32]. One crucial miRNA, miRNA-155, is upregulated when macrophages are transitioning from M2 to M1; M1 macrophages overexpressing miRNA-155 are generally more aggressive and are associated with tumor reduction [33]. Moreover, miRNA-342-5p has been found to foster a greater inflammatory response in macrophages by targeting Akt1 in mice. This miRNA also promotes the upregulation of Nos2 and IL-6, both of which act as inflammatory signals for macrophages [34]. Other miRNAs such as miRNA-125 and miRNA-378 have also been shown to be involved in the classical activation pathway of macrophages (M1) [35].

Classically activated macrophages are thought to play an important role in the recognition and destruction of cancer cells as their presence usually indicates good prognosis. After recognition, malignant cells can be destroyed by M1 macrophages through several mechanisms, which include contact-dependent phagocytosis and cytotoxicity (i.e. cytokine release such as TNF-α) [24]. Environmental signals such as the tumor microenvironment or tissue-resident cells, however, can polarize M1 macrophages to M2 macrophages. In vivo studies of murine macrophages have shown that macrophages are plastic in their cytokine and surface marker expression and that re-polarizing macrophages to an M1 phenotype in the presence of cancer can help the immune system reject tumors [19].

M2 Phenotype

M2 macrophages are anti-inflammatory and aid in the process of angiogenesis and tissue repair. They express scavenger receptors and produce large quantities of IL-10 and other anti-inflammatory cytokines [33, 36]. Expression of IL-10 by M2 macrophages promotes a Th2 response. Th2 cells consequently upregulate the production of IL-3 and IL-4. IL-3 stimulates proliferation of all cells in the myeloid lineage (granulocytes, monocytes, and dendritic cells), in conjunction with other cytokines, e.g., Erythropoietin (EPO), Granulocyte macrophage colony-stimulating factor (GM-CSF), and IL-6. IL-4 is an important cytokine in the healing process because it contributes to the production of the extracellular matrix [23]. M2 macrophages exhibit functions that may help tumor progression by allowing blood vessels to feed the malignant cells and thus promoting their growth. The presence of macrophages (thought to be M2) in the majority of solid tumors negatively correlates with treatment success and longer survival rates [37]. Additionally, the presence of M2 macrophages has been linked to the metastatic potential in breast cancer. Lin and colleagues found that early recruitment of macrophages to the breast tumor sites in mice increase angiogenesis and incidence of malignancy [38]. It is thought that the tumor microenvironment helps macrophages maintain an M2 phenotype [23, 39]. Anti-inflammatory signals present in the tumor microenvironment such as adiponectin and IL-10 can enhance an M2 response [41].

Tumor Associated Macrophages (TAMs)

Cells exposed to a tumor microenvironment behave differently. For example, tumor associated macrophages found in the periphery of solid tumors are thought to help promote tumor growth and metastasis, and have an M2-like phenotype [42]. Tumor associated macrophages can be either tissue resident macrophages or recruited macrophages derived from the bone marrow (macrophages that differentiate from monocytes to macrophages and migrate into tissue). A study by Cortez-Retamozo found that high numbers of TAM precursors in the spleen migrate to the tumor stroma, suggesting this organ as a TAM reservoir also [43]. TAM precursors found in the spleen were found to initiate migration through their CCR2 chemokine receptor [43]. Recent studies have found CSF-1 as the primary factor that attracts macrophages to the tumor periphery, and that CSF-1 production by cancer cells predicts lower survival rates and it indicates an overall poor prognosis [44-46]. Other cytokines such as TNF-α and IL-6 have been also linked to the accumulation/recruitment of macrophages to the tumor periphery [45].

It is thought that macrophages that are recruited around the tumor borders are regulated by an "angiogenic switch" that is activated in the tumor. The angiogenic switch is defined as the process by which the tumor develops a high density network of blood vessels that potentially allows the tumor to become metastatic, and is necessary for malignant transition. In a breast cancer mouse model, it was observed that the presence of macrophages was required for a full angiogenic switch. When macrophage maturation, migration, and accumulation around the tumor was delayed, the angiogenic switch was also delayed suggesting that the angiogenic switch does not occur in the absence of macrophages and that macrophage presence is necessary for malignancy progression [47]. Moreover, the tumor stromal cells produce chemokines such as CSF1, CCL2, CCL3, CCL5, and placental growth factor that will recruit macrophages to the tumor surroundings. These chemokines provide an environment for macrophages to activate the angiogenic switch, in which macrophages will produce high levels of IL-10, TGF-β, ARG-1 and low levels of IL-12, TNF-α, and IL-6. The level of expression of these cytokines suggests macrophages modulate immune evasion. It is important to note that macrophages are attracted to hypoxic tumor environments and will respond by producing hypoxia-inducible factor-1α (HIF-1α) and HIF-2α, which regulate the transcription of genes associated with angiogenesis. During the angiogenic switch, macrophages can also secrete VEGF (stimulated by the NF-κB pathway), which will promote blood vessel maturation and vascular permeability [48].

Tumor associated macrophages are thought to be able to maintain their M2-like phenotype by receiving polarization signals from malignant cells such as IL-1R and MyD88, which are mediated through IkB kinase β and NF-kB signaling cascade. Inhibition of NF-kB in TAMs promotes classical activation [40]. Moreover, another study suggested that p50 NF-kB subunit was involved in suppression of M1 macrophages, and reduction of inflammation promoted tumor growth. A p50 NF-κB knock-out mouse generated by Saccani et. al suggested that M1 aggressiveness was restored upon p50 NF-kB knockout, reducing tumor survival [49].

Because the tumor mass contains a great number of M2-like macrophages, TAMs can be used as a target for cancer treatment. Reducing the number of TAMs or polarizing them towards an M1 phenotype can help destroy cancer cells and impair tumor growth [50-52]. Luo and colleagues used a vaccine against legumain, a cysteine protease and stress protein upregulated in TAMs thought to be a potential tumor target [52]. When the vaccine against legumain was administered to mice, genes controlling angiogenesis were downregulated and tumor growth was halted [52].

Metabolism and Activation Pathways

Metabolic alterations present in tumor cells are controlled by the same genetic mutations that produce cancer [53]. As a result of these metabolic alterations, cancer cells are able to produce signals that can modify the polarization of macrophages and promote tumor growth [54, 55].

M1 and M2 macrophages demonstrate distinct metabolic patterns that reflect their dissimilar behaviors [56]. The M1 phenotype increases glycolysis and skews glucose metabolism towards the oxidative pentose phosphate pathway, thereby decreasing oxygen consumption and consequently producing large amounts of radical oxygen and nitrogen species as well as inflammatory cytokines such as TNF-α, IL-12, and IL-6 [56, 57]. The M2 phenotype increases fatty acid intake and oxidation, which decreases flux towards the pentose phosphate pathway while increasing the overall cell redox potential, consequently upregulating scavenger receptors and immunomodulatory cytokines such as IL-10 and TGF-β [56].

Multiple metabolic pathways play important roles in macrophage polarization. Protein kinases, such as Akt1 and Akt2, alter macrophage polarization by allowing cancer cells to survive, proliferate, and use an intermediary metabolism [58]. Other protein kinases can direct macrophage polarization through glucose metabolism by increasing glycolysis and decreasing oxygen consumption [57, 59]. Shu and colleagues were the first to visualize macrophage metabolism and immune response in vivo using a PET scan and a glucose analog [60].

L-arginine metabolism also exhibits discrete shifts important to cytokine expression in macrophages and exemplifies distinct metabolic pathways which alter TAM-tumor cell interactions [61]. Classically activated (M1) macrophages favor inducible nitric oxide synthase (iNOS). The iNOS pathway produces cytotoxic nitric oxide (NO), and consequently exhibits anti-tumor behavior. Alternatively activated (M2) macrophages have been shown to favor the arginase pathway and produce ureum and I-ornithine, which contribute to progressive tumor cell growth [61, 62].

Direct manipulation of metabolic pathways can alter macrophage polarization. The carbohydrate kinase-like protein (CARKL) protein, which plays a role in glucose metabolism, has been used to alter macrophage cytokine signatures [56, 57]. When CARKL is knocked down by RNAi, macrophages tend to adopt an M1-like metabolic pathway (metabolism skewed towards glycolysis and decreased oxygen consumption). When CARKL is overexpressed, macrophages adopt an M2-like metabolism (decreased glycolytic flux and more oxygen consumption) [56]. When macrophages adopt an M1-like metabolic state through LPS/TLR4 engagement, CARKL levels decrease, genes controlled by the NFκB pathway are activated (TNF-α, IL-12, and IL-6), and cell redox potential increases due to growing concentrations of NADH:NAD+ and GSH:GSSSG complexes. During an M2-like metabolic state, macrophages upregulate CARKL and genes regulated by STAT6/IL-4 (IL-10 and TGF-β).

Macrophage Immunotherapy Approaches Against Cancer

The role of cancer immunotherapy is to stimulate the immune system to recognize, reject, and destroy cancer cells. Cancer immunotherapy with monocytes/macrophages has the goal to polarize macrophages towards a pro-inflammatory response (M1), thus allowing the macrophages and other immune cells to destroy the tumor. Many cytokines and bacterial compounds can achieve this in vitro, although the side effects are typically too severe in vivo. The key is to find a compound with minimal or easily managed patient side effects. Immunotherapy using monocytes/macrophages has been used in past decades and new approaches are being developed every year [64, 65]. Early immunotherapy has established a good foundation for better cancer therapies and increased survival rate in patients treated with immunotherapies [66].

Some approaches to cancer immunotherapy include the use of cytokines or chemokines to recruit activated macrophages and other immune cells to the tumor site which allow for recognition and targeted destruction of the tumor site [67, 68]. IFN-α and IFN-β have been shown to inhibit tumor progression by inducing cell differentiation and apoptosis [69]. Also, IFN treatments are anti-proliferative and can increase S phase time in the cell cycle [70, 71]. Zhang and colleagues performed a study in nude mice using IFN-β gene therapy to target human prostate cancer cells. Their results indicate that adenoviral-delivered IFN-β gene therapy involves macrophages and helps suppress growth and metastasis [72].

The macrophage inhibitory factor (MIF) is another cytokine that can be used in cancer immunotherapy. MIF is usually found in solid tumors and indicates poor prognosis. MIF inhibits aggressive macrophage function and drives macrophages toward an M2 phenotype, which can aid tumor growth and progression. Simpson, Templeton & Cross (2012) found that MIF induces differentiation of myeloid cells, macrophage precursors, into a suppressive population of myeloid cells that express an M2 phenotype [73]. By targeting MIF, they were able to deplete this suppressive population of macrophages, inhibiting their growth and thus control tumor growth and metastasis [73].

The chemokine receptor type 2, CCR2, is crucial to the recruitment of monocytes to inflammatory sites and it has been shown as a target to prevent the recruitment of macrophages to the tumor site, angiogenesis, and metastasis. Sanford and colleagues (2013) studied a novel CCR2 inhibitor (PF-04136309) in a pancreatic mouse model, demonstrating that the CCR2 inhibitor depleted monocyte/macrophage recruitment to the tumor site, decreased tumor growth and metastasis, and increased antitumor immunity [74]. Another recent study by Schmall et al. showed that macrophages co-cultured with 10 different human lung cancers upregulated CCR2 expression. Moreover, they showed that tumor growth and metastatis were reduced in a lung mouse model treated with a CCR2 antagonist [75].

Other studies have used liposomes to deliver drugs to deplete M2 macrophages from tumors and to stop angiogenesis. Cancer cells that express high levels of IL-1β grow faster and induce more angiogenesis in vivo. Kimura and colleagues found that macrophages exposed to tumor cells expressing IL-1β produced higher levels of angiogenic factors and chemokines such as vascular endothelial growth factor A (VEG-A), IL-8, monocyte chemoattractant protein 1, etc., facilitating tumor growth and angiogenesis [76]. When they used clodronate liposomes to deplete macrophages, they found fewer IL-1β-producing tumor cells. They also found that by inhibiting NF-κB and AP-1 transcription factors in the cancer cells, tumor growth and angiogenesis were reduced. These findings may suggest that macrophages that surround the tumor site may be involved in promoting tumor growth and angiogenesis [76].

Compounds such as methionine enkephalin (MENK) have anti-tumor properties in vivo and in vitro. MENK has the ability to polarize M2 macrophages to M1 macrophages by downregulating CD206 and arginase-1 (M2 markers) while upregulating CD64, MHC-II, and the production of nitric oxide (M1 markers). MENK can also upregulate TNF-α and downregulate IL-10 [77].

Recent studies have focused on bisphosphonates as a potential inhibitor of M2 macrophages. Bisphosphonates are commonly used to treat metastatic breast cancer patients to prevent skeletal complications such as bone resorption [78]. While bisphosphonates stay in the body for short periods of time, bisphosphonates can target osteoclasts, cells in the same family as macrophages, due to their high affinity for hydroxyapatite. Once bisphosphonates bind to the bones, the bone matrix internalizes the bisphosphonates by endocytosis. Once in the cytoplasm, bisphosphonates can inhibit protein prenylation, an event that prevents integrin signaling and endosomal trafficking, thereby forcing the cell to go apoptotic. [69] Until recently, it was unknown whether bisphosphonates could target tumor associated macrophages but a recent study by Junankar et al. has shown that macrophages uptake nitrogen-containing bisphosphonate compounds by pinocytosis and phagocytosis, an event that does not occur in epithelial cells surrounding the tumor [79]. Forcing TAMs to go apoptotic using bisphosphonates could reduce angiogenesis and metastasis.

Additional approaches to cancer immunotherapy include the use of biomaterials that may elicit an immune response. Cationic polymers are used in immunotherapy because of their reactivity once dissolved in water. Chen et al. used cationic polymers including PEI, polylysine, cationic dextran and cationic gelatin to produce a strong Th1 immune response [77]. They were also able to induce proliferation of CD4+ cells and secretion of IL-12 typical of M1 macrophages [77]. Huang and colleagues also used biomaterials to trigger TAMs to produce an anti-tumor response by targeting TLR4 [80]. This study found that TAMs were able to polarize to an M1 phenotype and express IL-12. They found that these cationic molecules have direct tumoricidal activity and demonstrate tumor reduction in mice [80].

CAR T Cell Immunotherapy

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell; with transfer of their coding sequence facilitated by retroviral vectors.

Recently, therapies have been developed that utilize these engineered T cells to target and destroy cells containing cancer-specific or cancer-associated biomarkers. Once an adequate target is established, the extracellular domain of a T cell Receptor (TCR) is replaced with the single chain variable fragment (scFv) from an antibody against the target. This scFv contains the antibody variable region that determines binding. As a result, when in contact with the target, the scFv will bind and initiate signaling cascades that will activate the T cell. These engineered immune cells are termed Chimeric Antigen Receptors (CARs) due to their combinatorial nature and represent a novel new therapy in cancer treatment. Yet, CARs have been limited by the availability of adequate targets.

Chimeric antigen receptors (CARs) with extracellular antibody fragments directed against a tumor epitope fused to intracellular T-cell signaling domains, have been transduced into T cells, endowing them with a novel specificity toward a non-MHC restricted epitope[3]. Chimeric antigen receptors (CARs) are recombinant receptors that provide both surface antigen-binding and T-cell-activating functions. A number of CARs have been reported over the past decade, targeting an array of cell surface tumor antigens. Their biologic functions have dramatically changed following the introduction of tripartite receptors comprising a costimulatory domain, termed second-generation CARs. These have recently shown clinical benefit in patients treated with CD19-targeted autologous T cells. CARs may be combined with costimulatory ligands, chimeric costimulatory receptors, or cytokines to further enhance T-cell potency, specificity, and safety. CARs represent a new class of drugs with exciting potential for cancer immunotherapy.

T cells are capable of inducing potent anti-tumor responses, however, T cells that would most efficiently respond to peptide-MHC epitopes on the surface of tumors are often subjected to clonal tolerance or deletion, as many of these epitopes are very similar or identical to self-epitopes. T-cell therapies have involved genetic modification of T cells in vitro by introduction of TCRs against tumor-associated T-cell epitopes. This strategy has shown promise, but various challenges surrounding T-cell epitopes in general, as well as potential mispairing of introduced TCR with endogenous TCR, remain. There are proposals to harness the power of T cells in the fight against tumors, by allowing T cells to respond to traditional antibody epitopes.

BiTEs (Bispecific T-Cell Engagers)

Another strategy to target T cells to precise antibody epitopes takes advantage of a long-studied type of molecule called "bispecific antibody," which links an anti-cancer antibody with an antibody recognizing CD3 subunits. These have recently been termed BiTEs (bispecific T-cell engagers). A single-chain variable fragment (scFv) that binds a tumor epitope is linked to a second scFv that binds an invariant portion of the T-cell receptor complex, resulting in activation and targeting of effector T cells against the tumor epitope, regardless of the TCR-mediated specificity of the T cells. Evidence shows that these reagents are considerably more potent than antibodies against tumor cells alone. BiTEs have been constructed targeting more than ten tumor associated epitopes, including blinatumomab against CD19 (for B cell leukemias), and MT-110 against EpCAM (for various adenocarcinomas and cancer stem cells), both being currently evaluated in clinical trials. High response rates for relapse-free survival and elimination of minimal residual disease were found in refractory acute lymphoblastic leukemia (ALL) patients receiving blinatumomab in clinical trials.

Thymidine Kinase (TK1)

Human Thymidine Kinase 1 (TK1) is a well-known nucleotide salvage pathway enzyme that has largely been studied in the context of its overexpression in tumors. Since TK1 was initially popularized by its expression in the serum of cancer patients (sTK), its diagnostic and prognostic potential has been studied extensively. For example, several studies have demonstrated that sTK1 in many different cancer patients is elevated in a stage-like manner with a higher level of TK1 indicating a more advanced tumor [81].

Other studies have investigated the prognostic potential of TK1. One such study demonstrates that the TK1 levels in primary breast tumors can be used to predict recurrence. Other exciting TK1 prognostic studies show significant reductions in sTK1 levels when patients respond to treatment while sTK1 levels continue to rise in patients who do not appear to respond to their treatment. It is also known that sTK1 levels begin to rise prior to recurrence and noted in some cases sTK1 levels could predict recurrence "1-6 months before the onset of clinical symptoms". Several other studies confirm the rich potential of TK1 as a diagnostic and prognostic indicator of cancer [82].

Although the diagnostic and prognostic potential of TK1 has been well established, the therapeutic potential of TK1 remains veiled in comparison. While it is true that HSV-TK has been used in gene therapy and PET imaging utilizes TK1 to identify proliferating cancer cells, few, if any studies address the possibility of a TK1 immunotherapy. Perhaps this is primarily because TK1 is a known cytosolic protein. It has been recently discovered that TK1 is expressed not only in cancer cells but also on the surface membrane of most tumor types and is therefore a very viable target for tumor immunotherapy.

The diagnostic and prognostic potential of TK1 has been demonstrated using the traditional TK activity radioassay for both haematological malignancies and solid tumors. TK1 has been extensively studied in the context of cancer diagnostic biomarkers, where it has been shown to be upregulated in tissue and serum in both solid tumors and haematological malignancies.

TK1 levels in serum have also been shown to have diagnostic potential in other cancers such as bladder, cervical carcinoma, gastric, non-small cell lung, and renal and colorectal cancers. In summary, high TK1 serum levels correlate with tumor aggressiveness and can be indicative of early events in carcinogenesis. However, the mechanism by which TK1 enters the serum and its function in the serum has been largely unexplored. Perhaps, its function in the serum is connected to regulating the immune system. Further analyses are needed to understand this connection and its significance.

Human TK1 (hTK1) as a monomer, in its most basic structure, is 234 amino acids in length with a molecular weight of 25.5 kDa. TK1 adopts a variety of oligomeric forms although it is most commonly found as a dimer or tetramer, approximately 53 kDa and 100 kDa respectively. In 1993, Munch-Petersen reported that the TK1 dimer was the low-efficiency form of the enzyme with a high Km (15 µM). On the other hand, the TK1 tetramer was a high-efficiency form with a low Km (0.7 µM) and was reported to have 30-fold increased efficiency compared to the dimer in catalyzing its phosphoryl transfer reaction. The crystallization of TK1 indicates that the tetrameric form is composed of a dimer of dimers. As such, there are two distinct monomer-monomer interfaces labeled strong and weak. The weak interface is primarily stabilized indirectly by ATP, the donor molecule, while the strong interface is stabilized directly through many polar interactions. Each monomeric has an α/β-domain which is most similar to DNA binding proteins including RecA.

Thymidine kinase 1 (TK1) is a nucleotide salvage pathway enzyme primarily responsible for converting deoxythymidine to deoxythymidine monophosphate, and it is highly upregulated during cellular replication. During DNA synthesis, nucleotides are either synthesized de novo or through the salvage pathway where they are recycled from intracellular and extracellular sources.

TK1 is one of two major salvage pathway kinases responsible for maintaining the cellular nucleotide pool. TK1 is primarily responsible for the phosphorylation of deoxythymidine (dT). Its product, dTMP, is then subsequently phosphorylated and incorporated into the DNA as deoxythymidine triphosphate (dTTP). Expectedly, dTTP helps to regulate this process as it inhibits TK1, the rate-limiting step of this process. Under normal proliferating conditions, TK1 is regulated by the cell cycle. TK1 levels are very low or barely detectable during G1 phase and begin to increase during late G1 phase. TK1 levels peak during S phase at concentrations near 200 nM, at least 10-fold higher than levels during G1 phase. Interestingly, Sherley et al. reported that under normal conditions, TK1 mRNA only increased 3-fold or less, compared to the 15-fold increase in protein activity levels, during the cell cycle. They also determined that the rate of [35S] incorporation during S phase was 12-fold more efficient than during the G1 phase. Indicating that the rapid increase in TK1 levels during S phase was a result of an increase in the efficiency of TK1 translation, rather than an increase in transcription. This finding is particularly interesting in light of a study by Chou et al. in which a 5'-untranslated region (5'UTR) allowed translation of TK1 mRNA to be cap-independent. Munch-Peterson et al. has since demonstrated that this rapid increase in TK1 is also a result of conversion from an inactive dimeric to the active tetrameric TK1 form. Several studies confirm that TK1 levels increase as a result of DNA damage, especially following irradiation or chemotherapy.

In 2010, Chen et al. further characterized the connection between TK1 and DNA damage by showing p53−/− tumor cells increased TK1 levels in response to DNA damage while p53 wildtype tumor cells did not. This connection between TK1 and p53 has been corroborated in other studies which report normal p53 function is required to maintain cell cycle dependent regulation of TK1, and upon p53 loss, there is a compensatory increase in TK1. Closer analysis of this connection revealed that the increase in TK1 levels following DNA damage is dependent on p21. In fact, Huang et al. (2001) showed that the c-terminal domain of p21 interacts with TK1 and overexpression of TK1 prevents p21-dependent growth suppression. These results challenged the traditional role of TK1 in tumor cells. For example, Chen et al. determined that TK1 knockdown did not affect the growth of tumor cells, even though the levels of dTTP significantly decreased (p<0.01). Their results support the conclusion that the primary role of TK1 in tumor cells is DNA repair rather than to provide sufficient dTTP levels for replication and growth. This conclusion is supported, however the biochemical role of TK1 is still not clear. In normal cells, TK1 is responsible for maintaining the dTTP nucleotide pool in a cell cycle-dependent manner. Additionally, TK1 plays an invaluable role in DNA repair and survival of tumor cells following DNA damage. The biological significance of TK1 is less understood and somewhat puzzling. Normal TK1 function is essential for proper development and function of the kidney and salivary gland although these mechanisms are not understood. TK1 also appears to be necessary for the normal function of the immune system and may play a role in its deregulation. Another unexplored and puzzling function of TK1 is its role in the circulatory system of cancer patients.

Hypoxanthine Guanine Phosphoribosyltransferase (HPRT).

HGPRT or HPRT is a crucial enzyme for the large-scale production of Guanine and Inosine bases. HPRT functions by transferring phosphoribose from PRPP to hypoxanthine or guanine bases to form IMP and GMP respectively. Due to its role in DNA maintenance HGPRT is known as a housekeeping gene and is often used as a standard for quantitative analysis because of its constant expression within all eukaryotic cells.

Hypoxanthine-guanine phosphoribosyltransferase (HGPRT) is an enzyme encoded in humans by the HPRT1 locus. This enzyme that allows cells to recycle purines, a type of building block of DNA and its chemical cousin RNA. Manufacturing purines uses more energy and takes more time than recycling purines, which makes recycling these molecules more efficient. Recycling purines ensures that cells have a plentiful supply of building blocks for the production of DNA and RNA. The process of recycling purines is also known as the purine salvage pathway.

Hypoxanthine Phosphoribosyltransferase 1 (HGPRT)

Also critical to the production of nucleotides utilized in cellular division and successful DNA replication, Hypoxanthine Guanine Phosphoribosyltransferase (HPRT or HGPRT) is an important enzyme for the large-scale production of guanine and inosine in the purine salvage pathway. Salvage pathway enzymes act as recycling agents, utilizing the components of old nucleotides to bypass the expenditure of energy required for nucleotide synthesis. This production method dominates a majority of the cell cycle in humans because 90% of free purines are recycled. As a critical enzyme in this process, HPRT is essential to the survival and propagation of cells. Yet, its role in the proliferative capacity of cancer cells remains largely unknown. Through initial work evaluating this relationship, preliminary data suggest that cancer cells may upregulate HPRT and exclusively present the protein on the surface of the cell.

Hypoxanthine Guanine Phosphoribosyltransferase (HGPRT) is a salvage pathway enzyme involved in the purine synthesis of Guanine and Inosine (Caskey & Kruh, 1979). HGPRT is a transferase that will cleave the ribose monophosphate from PRPP and covalently attach it to a guanine base to form GMP. Once the ribose monophosphate has been released from PRPP it releases pyrophosphate (PPi) as a byproduct. As GMP is created, additional enzymes will incorporate more phosphate groups to form functional GTP. This same process is also consistent with inosine nucleotide synthesis as HGPRT will transfer the ribose monophosphate from PRPP to a hypoxanthine base to form IMP. This enzyme transfers phosphoribose from PRPP to hypoxanthine or guanine bases (Stout & Caskey, 1985; Wilson, Tarrt, & Kelley, 1983). The HGPRT enzyme is composed of ten beta strands and six alpha helices with residues 37-189 forming the core of the enzyme (Eads, Scapin, Xu, Grubmeyer, & Sacchettini, 1994). Depending on the pH of the surrounding tissue, the protein can exist as either a dimer or a tetramer with identical subunits (Eads et al., 1994; Keough, Brereton, De Jersey, & Guddat, 2005; Zhang et al., 2016). The molecular weight of each of the protein subunits is 48.8783 kDa and the molecule has an instability index of 21.69, which classifies the protein as stable. The homo tetramer contains four subunits labeled A, A', B, and B' (Eads et al., 1994).

Shown in FIG. 8 is the HGPRT biochemical pathway. The homo tetramer structure of human HGPRT has beta sheets, beta strands, alpha helices, and beta turns. The protein has only 27% alpha helices and 27% beta sheets, which indicates that the remaining 46% of the enzyme are beta turns and random coils. The structure has subunits labeled, A, A' and B, B'. Each subunit is relatively identical and is translated from the same mRNA message.

The enzyme has several regions that each have distinct functions in substrate recognition and reactivity. The carboxy terminal end of the central beta sheet is primarily involved in substrate recognition. The core region of the protein contains twisted parallel beta sheets with five beta strands that are surrounded by four alpha helices. Resides 65-74 form the most flexible portion of the protein as they create a loop that will bind pyrophosphate. The residues of the enzyme that will bind PRPP substrate are 129-140, which are located on the floor of the active site. In order for enzymatic activity in the active site to be successful the metal ion $Mg^{2+}$ is required (Eads et al., 1994; Zhang et al., 2016).

The gene that encodes HGPRT is called HPRT. This 47,827 bp gene resides on the long arm of the X chromosome and is relatively large, especially considering that only a small portion of the transcribed DNA is eventually translated. The gene contains 9 exons that code for a 217 amino acid protein, which represents only 1.3% of the original genomic message (Fuscoe, Fenwick, Ledbetter, & Caskey, 1983; Stout & Caskey, 1985; Wilson et al., 1983). Because the final protein product is involved in cellular maintenance, the control sequences upstream of the HPRT gene contain the hallmarks of a mammalian housekeeping gene; there is an absence of 5' transcriptional sequences including the TATA and CAAT boxes and there are exceptionally GC-rich sequences with many GC hexanucleotide motifs along the 5' end of the gene (Kim et al., 1986). As a housekeeping gene, HPRT is found in all somatic tissue in low levels (Melton, Mcewan, Reid, & Mckie, 1986). In a majority of human cells HPRT mRNA transcripts comprise only 0.005 to 0.01% of the total mRNA (Caskey, 1981). The only exception is in central nervous tissue where there is an unusually elevated level of HPRT expression ranging from 0.02 to 0.04% of the total mRNA, which is a 4 fold increase in comparison to other somatic tissue (Caskey, 1981; Zoref-shani, Frishberg, & Bromberg, 2000). This elevated expression is not fully understood because cells in the central nervous system (CNS) are not stimulated to divide and would therefore require less machinery for nucleotide synthesis. In addition, the human genome contains non-functional HPRT homologous regions in the autosomal DNA of chromosomes 5, 11, and 13 (Fuscoe et al., 1983). These DNA sequences are not known to be transcribed and are most likely pseudogenes, but their exact origin and expression is not well understood (Nyhan & Diego, 2012).

Because of the proliferative capabilities of cancer cells and the large demand for nucleotide production, it is expected that HPRT would be upregulated in these environments (Linehan & Goedegebuure, 2005). Through preliminary studies to determine whether HPRT is upregulated in a cancerous setting, it has been determined that there is a strong association between HPRT and the plasma membrane of cancer cells. This association has been observed in a variety of cancer types and cell lines with multiple different assays. Confocal images and flow cytometry analysis have been obtained for multiple different cancer cell lines and show that HPRT is consistently expressed on the surface of all cancer types tested. This same expression is not observed for the salvage pathway enzymes DCK and APRT, indicating that HPRT has a role in a cancerous environment that is not shared by all salvage pathway enzymes. The reason for this surface expression is not known, and one can only speculate to why it would be presented externally in cancer. It is possible that this unique surface expression may point to a secondary role of HGPRT that goes beyond its primary role as a purine synthesis enzyme and provide additional information about unique ecosystem of the tumor microenvironment.

SUMMARY

Significant factors for the success of present system for cancer therapy include modification of macrophages with chimeric antigen receptors (MOTO-CARs), and tumor antigens are associated with cancer cells and not with normal cells.

Macrophages

An aspect is the use of modified macrophages against the cancer antigens. Using CAR technology, macrophages have antigen receptors against cancer antigens.

As noted above CAR technology has been used to develop T-cells with antigen receptors against cancer antigens. These antigens are often substances that in normal condition don't activate an immune response, because they are identical or similar to human-produced substances. For this reason, T-cells have been modified to have such receptors. Therapies have been studied that involve such T-cells with chimeric antigen receptors (CAR), where the antigen receptors are directed against a tumor epitope. The T cells are capable of inducing potent anti-tumor responses, as noted in the Background above, these therapies are promising, but there are problems that have appeared.

For example, is has been found that normal T cells that would most efficiently respond to peptide-MHC epitopes on the surface of tumors are often subjected to clonal tolerance or deletion, as many of these epitopes are very similar or identical to self-epitopes. T-cell therapies have involved genetic modification of T cells in vitro by introduction of TCRs against tumor-associated T-cell epitopes. This strategy has shown promise, but various challenges surrounding T-cell epitopes in general, as well as potential mispairing of introduced TCR with endogenous TCR, remain. There are proposals to harness the power of T cells in the fight against tumors, by allowing T cells to respond to traditional antibody epitopes.

T-cells can be long-lived and be present indefinitely in the in the body, and can also be antigen-experienced against the cancer antigen. This means that T-cells that are antigen-specific against the tumor antigen marker can be present after the therapy treatment and elimination of the cancer. This can be a problem because the tumor-antigens are usually human created (necessitating the CARs in the first place) and may be present in small amounts for different body functions. Continued existence of the modified CAR T-cells and the potential innocent occurrence of the target antigen may result in harmful and unwanted activation of the T-cells. This may compromise an important process in the body, or lead to a cytokine storm, where breakdown of the cytokine production/activation feed-back loop for T-cells results in uncontrolled and ballooning activation of immune cells, resulting in a massive immune response. A cytokine storm can do significant damage and potentially result in death.

The problem is solved in the present therapy system by modifying macrophage cells to create Macrophage CAR (MOTO-CAR) cells against the cancer antigen. Macrophage cells, although they may last several weeks after an infection, and do not appear to possess memory, unlike CAR T cells. Accordingly, potential harm from a response to innocent low concentrations of the cancer antigen by lingering CARs will diminish. In addition, macrophages do not participate in the cytokine storm phenomena, and eliminate the problem present with T-Cell CARs.

Antigens Associated with Cancers

An aspect of the present therapy is that certain cancer and tumor antigens are associated with cancers and tumors, and are not associated with non-cancerous tissues. For example, It has been demonstrated that TK1 and HGPRT are expressed on the surfaces of many, and likely all, cancerous types, with little or no expression on the surface of normal cells. These provide an antigen marker that allows a therapy to detect and target cancer cells, and kill the cancerous cells without harming non-cancerous cells.

An aspect is the use of monocytes/macrophages to combat cancer by combining modified macrophage-specific CAR technology and human/humanized antibodies against human thymidine kinase 1 (TK1) and Hypoxanthine-guanine phosphoribosyl transferase (HPRT). It also includes the use of humanized antibodies against other common tumor targets such as CD19, CD20, epidermal growth factor (EGFR), receptor tyrosine kinase-like orphan receptor 1 (ROR1) and other novel tumor targets to produce a macrophage potentially activated against many different tumors.

It is believed that there are additional potential antigen markers that can be used by the present therapy system to target cancer cells over normal cells. These may include, for example, salvage pathway enzymes, substance that contribute to metastasis such as those that assist in blood vessel formation. Any normal antigen that is not found on the surface of normal cells but may be expressed on the surface of cancer cells, any mutated normal human protein that may be significantly different from normal protein so as to be distinguished by CAR or MOTO CAR. Some fetal antigens that may be expressed exclusively on cancer cells, mutated proteins produced as a result of tumor formation may also be used as targets if they are sufficiently different from the non-mutated protein so as to be distinguished by antibodies.

Both TK1 and HPRT are up regulated in many forms of cancer and have been found on the surface of many cancer cells. Neither is found on the surface of normal cells and therefore is a prime target for immunotherapy. Preliminary findings indicate that HGPRT is on the surface in the same proportion as TK1 i.e. if TK1 is high HGPRT is also high, if TK1 is low HGPRT is also low. While not being bound to a theory, they may be complexed together.

The present technology contemplates the use of a CAR or BiTE produced with a scFv from a humanized or non-human mammal (such as mouse) monoclonal antibody to HGPRT or TK1, that could be used with appropriate genetic engineering to manipulate macrophages ultimately from a patient but not limited to such, to treat a disease such as cancer. The fact that antigen substances, (e.g. TK1, HGPRT) are on the surface of cancer cells and not on the surface of any normal cell is a major part of the discovery, as this knowledge can be used to allow the macrophages to be directed specifically to the tumor cells.

The uniqueness of the present technology lies in part in the fact that using specifically generated antibodies to human cancer antigens that are associated with cancer cells and not normal cells can be used to target tumors. For example, antigens expressed in this manner on the surface of the cancer cell, like TK1 and HGPRT can be used to target CARs, MOTO CARs and BiTEs to the tumors.

Antibodies specific to human HGPRT are known, such as at http://www.abcam.com/hprt-antibody-ab10479.html, "Anti-HPRT antibody (ab10479)"

Antibodies specific to human TK are known, such as disclosed in U.S. Pat. Nos. 9,267,948, 7,837,998, 7,311,906, and 5,698,409

An aspect is using a macrophage or a monocyte or other immune cell containing a MOTO-CAR Vector (scFV fused to a Toll like receptor intracellular activating region) designed against as specific tumor associated antigen, and using monocytes or macrophages and a MOTO-CAR technology against tumors or other diseases. The technology could be used against any specific antigen using vectors to illicit an immune response utilizing monocytes or macrophages.

An aspect is using a macrophage or a monocyte or other immune cell containing a MOTO-CAR Vector (scFV fused to a Toll like receptor intracellular activating region) designed against as specific tumor associated antigen such as TK1 and HPRT.

An aspect is a method for treating tumors where the specific tumor antigen is in particular HPRT. TK1 has high levels in serum from patients with aggressive tumors this could bind to the MOTO-CAR and activate the CAR before it gets to the tumor site. HPRT has been shown to have low serum levels and also seems to be more abundantly dispersed on the cancer cell membranes and not on normal cells.

An aspect is a method for polarizing macrophages to an M1 phenotype in a cancerous environment. The MOTO-CAR is designed to attach to TK1 or HPRT on the surface of cancer cells and activate the macrophage converting it to a M1 aggressive killing macrophage as opposed to the M2 that associates with the tumor and protects it from immune destruction.

An aspect is use of macrophage specific promoter for macrophage CAR activation. Since the MOTO-CAR may bind soluble TK1 in the serum it could activate without being near the tumor. A possible solution to this is to separate monocytes from the patient and infect them with a MOTO-CAR construct that will be under the control of a macrophage specific promoter. Monocytes only become macrophages when they move from the blood to the tissues. Having the MOTO-CAR under the control of a macrophage specific promoter will allow the MOTO-CAR only to be expressed in tissue and thereby avoid the problems with activation in serum.

Another aspect is utilizing cytoplasmic macrophage activating molecules/signaling cascades such as Toll like receptors. The MOTO-CAR may be activated by utilizing the Toll like receptor cytoplasmic domain. There are other activating signaling molecules that can have a similar function. And a different activating molecule is contemplated. The molecule used does not have to be a Toll like Receptor there are other signaling pathways that could utilize this technology.

Another aspect involves utilizing an scFv derived from a human/humanized monoclonal, Use of scFv's from mouse or human are contemplated. Such as, for example, MOTO-CAR with scFv's (Specific to TK1) from both mouse and human, or obtaining human antibodies against TK1 and HPRT using a yeast library that produces human monoclonal antibodies.

Another aspect is the use of this technology to target diseases such as cancer and further developments for use for other diseases (i.e. infectious disease and autoimmune diseases). MOTO-CAR technology may not be limited to attacking cancer, and there may be other diseases where this technology could be effective.

Another aspect is use of co-stimulatory molecules to enhance the macrophage activation. (MD2, CD14) Other molecules could be used that are involved in macrophage activation as part of the MOTO-CAR construct. Most immune cells require stimulation from other molecules before they fully activate. In some applications, for the MOTO-CAR to become fully activated it may require the co activation of accessory molecules. These molecule may include (but are not limited to) MD-2 and CD 14.

Another aspect is use of bispecific macrophage engagers (BIME) for use in immunotherapy. Additional to the MOTO-CAR a technology called Bispecific Macrophage Engagers (BIMEs) may be utilized. BIME takes advantage of macrophage activation and novel tumor antigens. It involves the union of a macrophage activator protein or ScFv linked by an amino acid spacer to a ScFv against a tumor antigen. As examples, are three different illustrative BIMEs. The first is a molecule composed of a molecule of IFN-γ linked by an amino acid spacer to any ScFv against TK1, HPRT or any other tumor antigen. The second is designed by the union of a ScFv against the CSF-1 receptor and a ScFv against a tumor antigen. The third involves a bispecific antibody against the hydrophobic pocket of the MD2 protein, which brings in close activation proximity two TLR4 proteins triggering the signaling cascade by the physical encounter of the two TLR4s's TIR domains in the cytosol. MOTO-CARS and BIMES are part of the new generation of cancer immunotherapy technologies and both of them could be used to in the treatment of many different cancer types.

DETAILED DESCRIPTION

Figure 1:
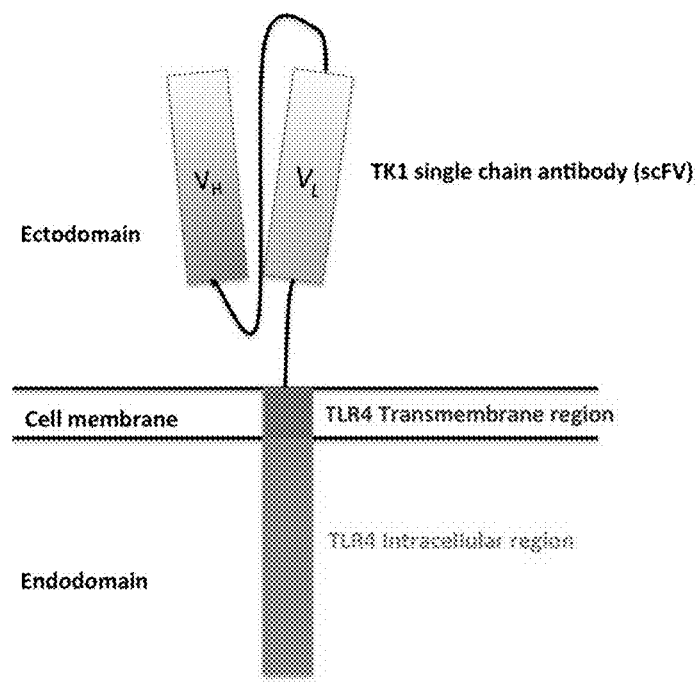
FIG. 1 is a schematic illustrating a macrophage chimeric antigen receptor
Figure 2:
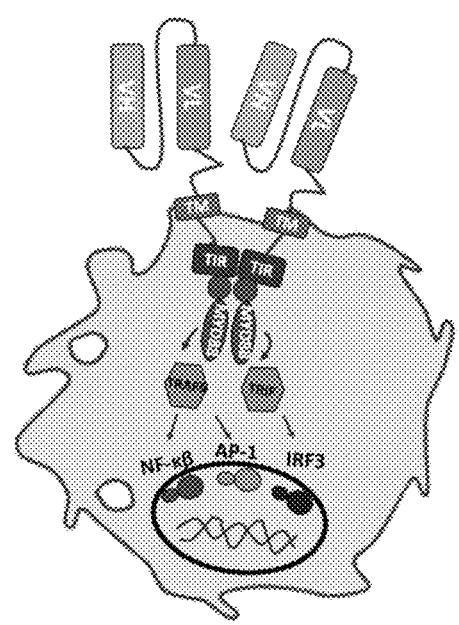
FIG. 2 is a schematic showing a Macrophage Toll-like receptor CAR. (MOTO CAR). The intracellular domain and transmembrane domain of Toll like receptors, FC-gamma III receptor, IL-1 or the IFN-gamma receptors can be fused to a suitable hinge and a ScFv against a tumor antigen to activate Macrophages upon binding to a specific tumor antigen.
Figure 3A:
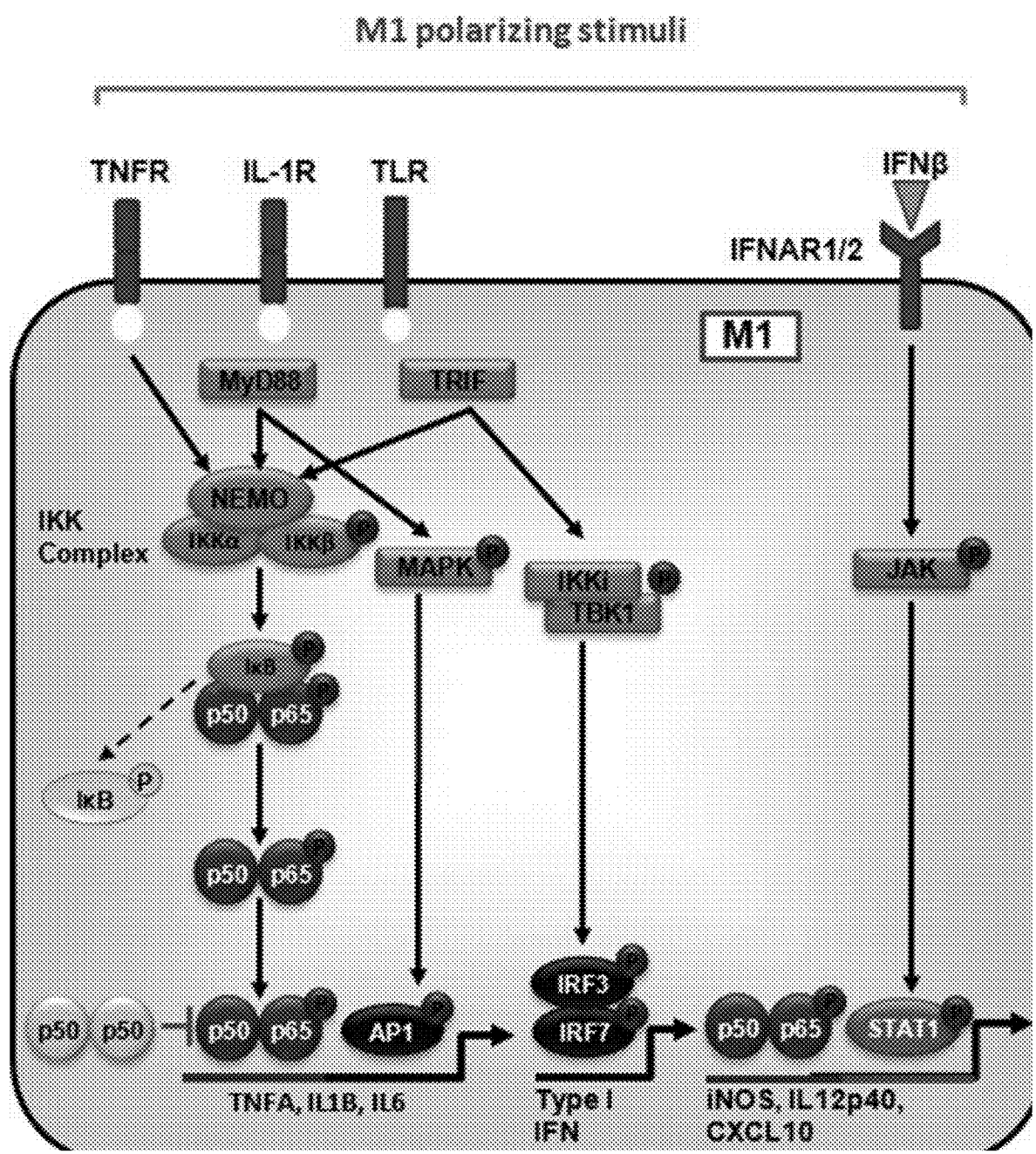
FIG. 3a is a schematic showing different macrophage receptors that could be utilized to build a macrophage CAR.
Figure 3B:
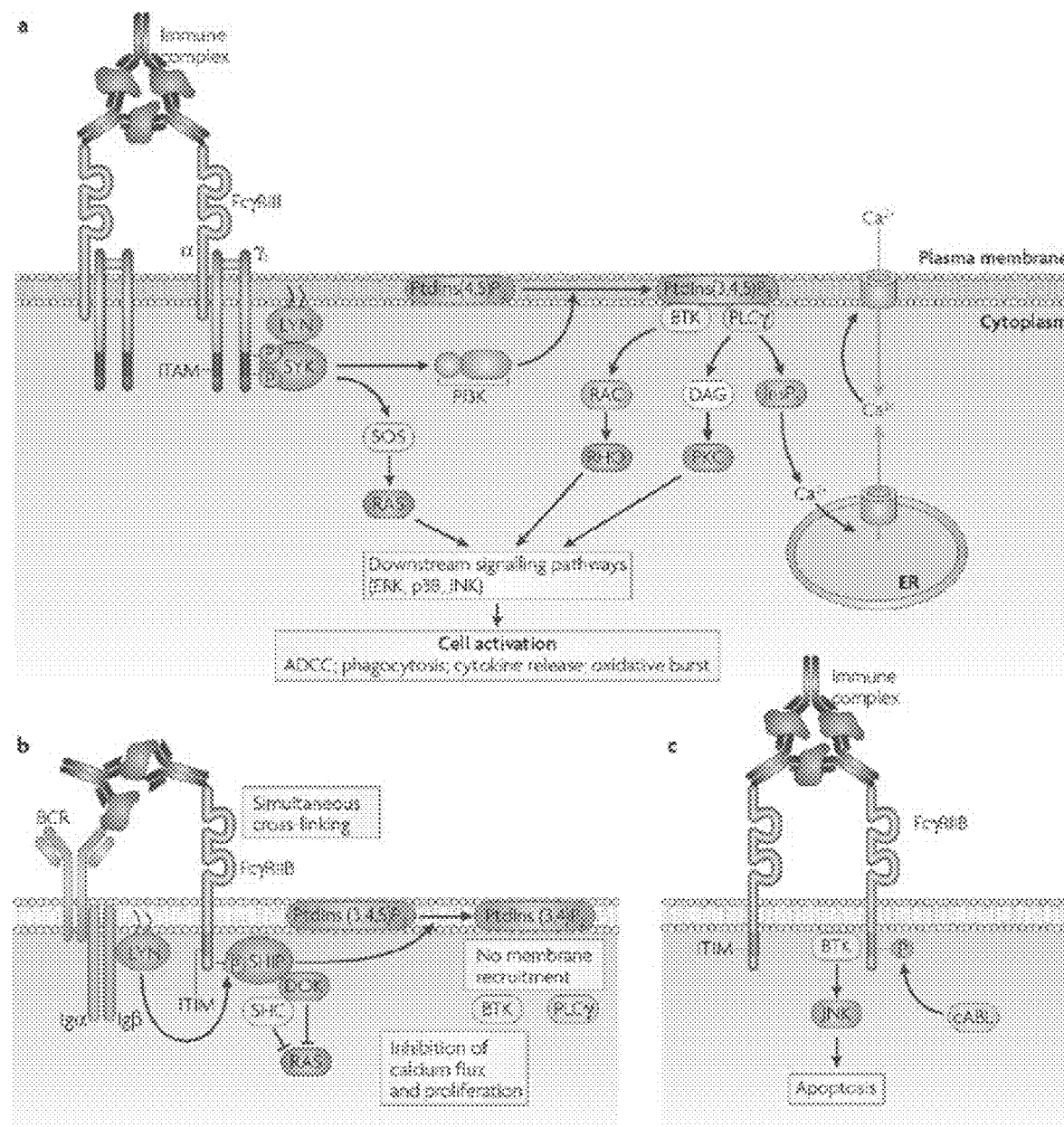
FIG. 3b is a schematic showing signaling of Fc Gamma Receptor III
Figure 4:
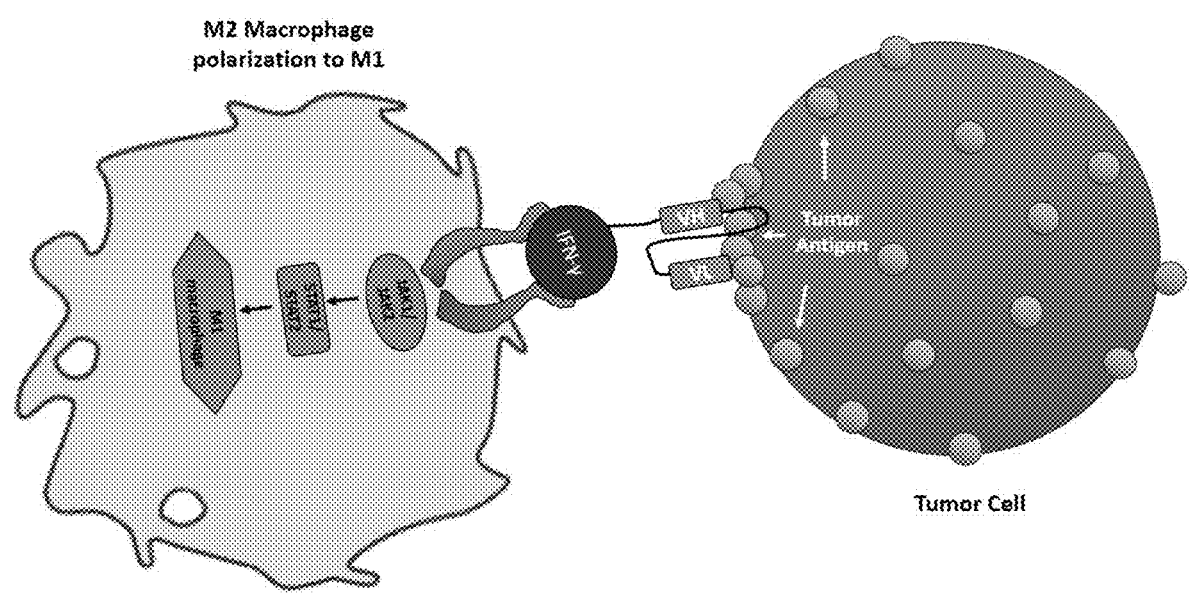
FIG. 4 is a schematic showing where Bispecific Macrophage Engager$_{IFN-\gamma}$ (BIME$_{IFN-\gamma}$). M2 tumor resident macrophages can be polarized and anchored to tumor cells using a molecule of IFN-γ linked by a aminoacid spacer to a ScFv against a tumor antigen.
Figure 5:
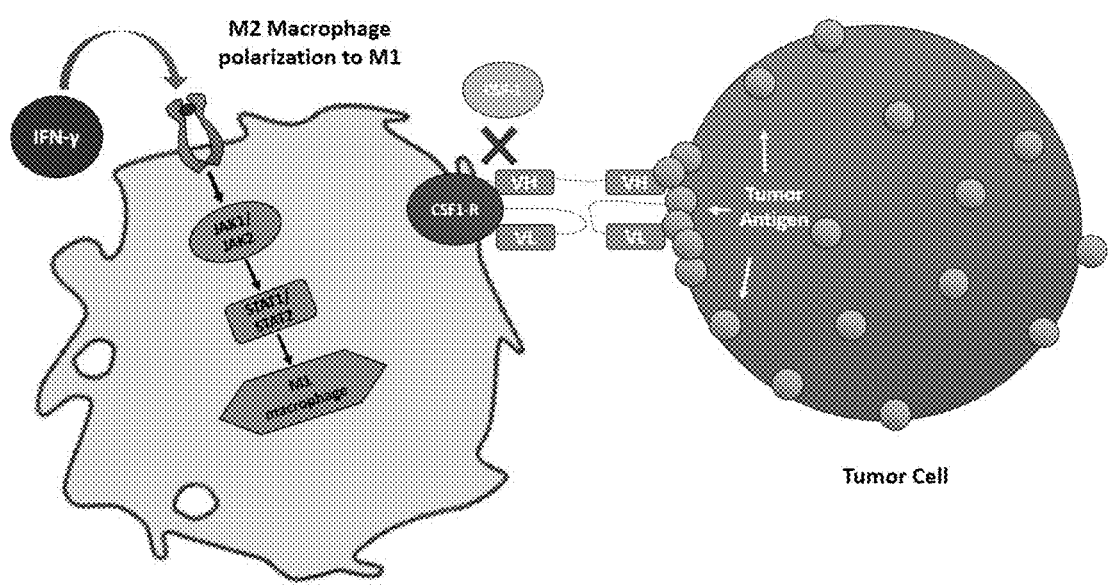
FIG. 5 is a schematic showing where Bispecific Macrophage Engager (BIME). M2 macrophages can be polarized towards M1 phenotype and directed to tumor cells. A bispecific antibody can block CSF-1 receptor blocking CSF-1 a receptor that leads to an M2 profile At the same time, the macrophage can be anchored with a ScFv against a tumor antigen. The patient then can receive IFN-γ and the macrophage can be polarized towards a M1 phenotype for tumor elimination.
Figure 6:
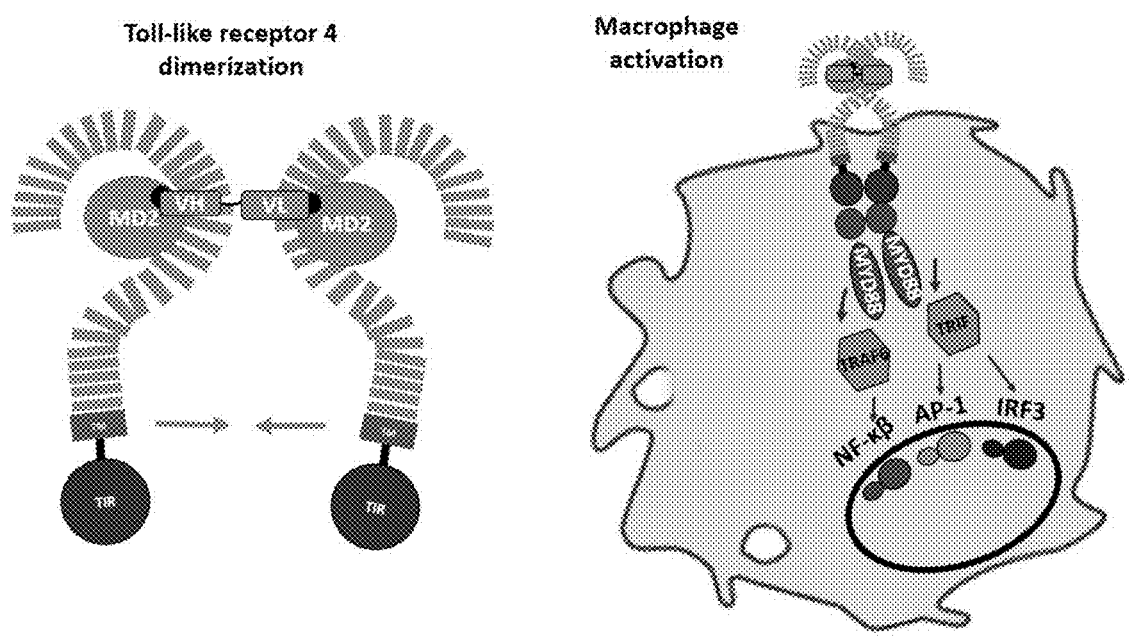
FIG. 6 is a schematic showing Macrophage Activator$_{MD2}$ (BIME$_{MD2}$). Toll-like receptor 4 dimerization can be triggered by using a ScFv against the hydrophobic pocket of the MD2 protein. Then a BIME can be added to anchor macrophages to the tumor cells.
Figure 7:
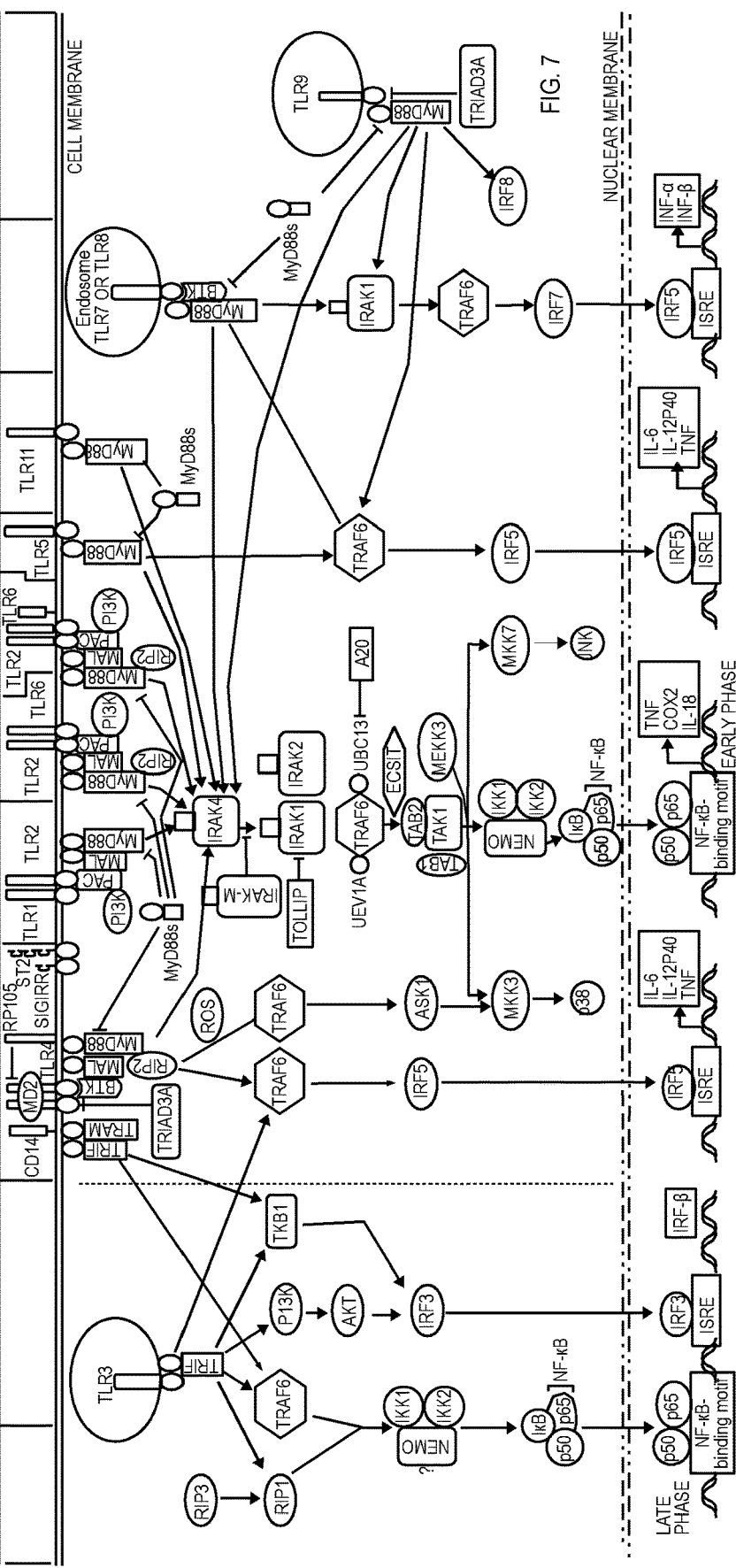
FIG. 7 is a schematic illustrating Toll Like Receptor Signaling
Figure 8:
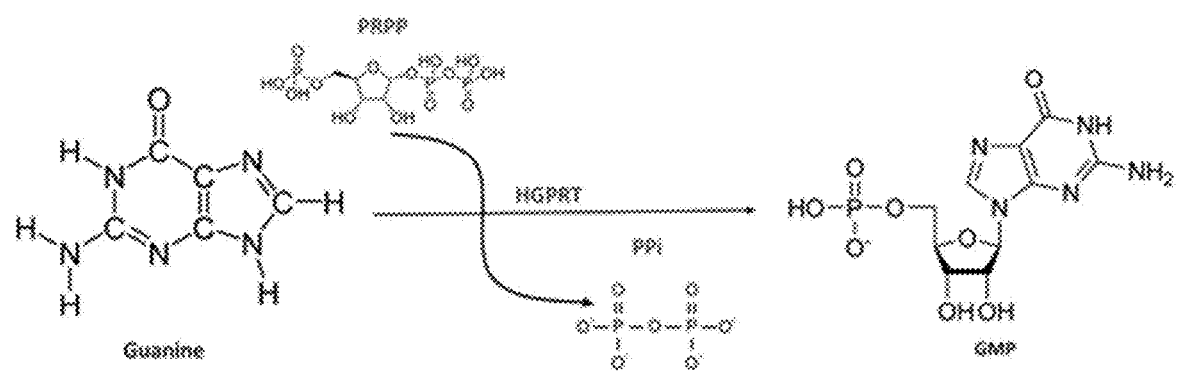
FIG. 8 is shown the HGPRT biochemical pathway

TK1 and HPRT are exclusively expressed on the surface membrane of tumor cells and have led to the development of a range of monoclonal antibodies against human TK1 and HPRT. The specific binding capacity of these specific monoclonal antibodies could be used in macrophages transfected with a modified macrophage-specific chimeric antigen receptor to treat cancer patients. A method for modifying a monocyte/macrophage to have receptors against human TK1 (MOTO CAR) might include producing human/humanized monoclonal antibodies that are TK1 and HPRT specific (FIG. 1). These TK1 and HPRT specific monoclonal antibodies would be used to create chimeric antigen receptors (CARs) by fusion of the single-chain variable fragments to macrophage (MO) signaling domains (FIG. 2) (such as the cytoplasmic domain portion from a toll-like receptor (TO), the FC gamma III, IL-1 or INF-gamma receptors) (FIG. 7) that would be transduced into the macrophage (FIG. 3a,b). The premise is that monocytes/macrophages would be removed from the patient and transfected ex vivo with a macrophage-specific chimeric antigen receptor lentiviral vector. This will allow the macrophage to recognize and bind to cells expressing TK1, HPRT or any other tumor antigen on their surface membrane, stimulating macrophage activation and cancer cell death. This could be used to treat many different types of cancer as TK1 is present on the surface of many different tumors and is not found on the surface of normal cells.

MOTO-CAR Construction cDNA was purified from a monoclonal antibody hybridoma cell (CB1) with an antibody specific to human TK1 and used to amplify the heavy and light chains of the CB1 variable region via polymerase chain reaction (PCR) Sequences from the heavy and light chain were confirmed using NCBI Blast. CB1 heavy and light chains were fused together via site overlap extension (SOE) PCR to make a single chain fragment variable (scFv) using a G4S linker. The G4S linker was codon optimized for yeast and humans using the Codon Optimization tool provided by IDT (https://www.idtdna.com/CodonOpt) in order to maximize protein expression. The CB1 scFv was cut using restriction enzymes and inserted into a pMP71 CAR vector.

TK-1 and HPRT-specific human scFv antibodies were isolated from a yeast antibody library. TK-1 and HPRT protein was isolated, His-tagged, and purified. TK-1 and HPRT protein was labeled with an anti-His biotinylated antibody and added to the library to select for TK-1 and HPRT-specific antibody clones. TK-1 and HPRT antibody clones were alternately stained with streptavidin or anti-biotin microbeads and enriched using a magnetic column. Two additional rounds of sorting and selection were performed to isolate TK-1 and HPRT specific antibodies. For the final selection, possible TK-1 and HPRT antibody clones and their respective protein were sorted by fluorescence-activated cell sorting (FACS) by alternately labeling with fluorescently-conjugated anti-HA or anti-c-myc antibodies to isolate TK-1 and HPRT specific antibodies. High affinity clones were selected for CAR construction. Other human antibodies or humanized antibodies from other animals could be selected or altered to be TK-1 or HPRT specific by using phage display or other recombination methods.

Selected scFv clones were then combined with human IgG1 constant domains to create an antibody for use in applications such as Western blot or ELIZA in order to confirm the binding specificity of the scFv. The antibody construct was inserted into the pPNL9 yeast secretion vector and YVH10 yeast were transformed with the construct and induced to produce the antibody. Other expression systems such as E. coli or mammalian systems could also be used to secrete antibodies.

Isolation and Characterization of Protein-Specific Antibody Fragments.

Figure 9:
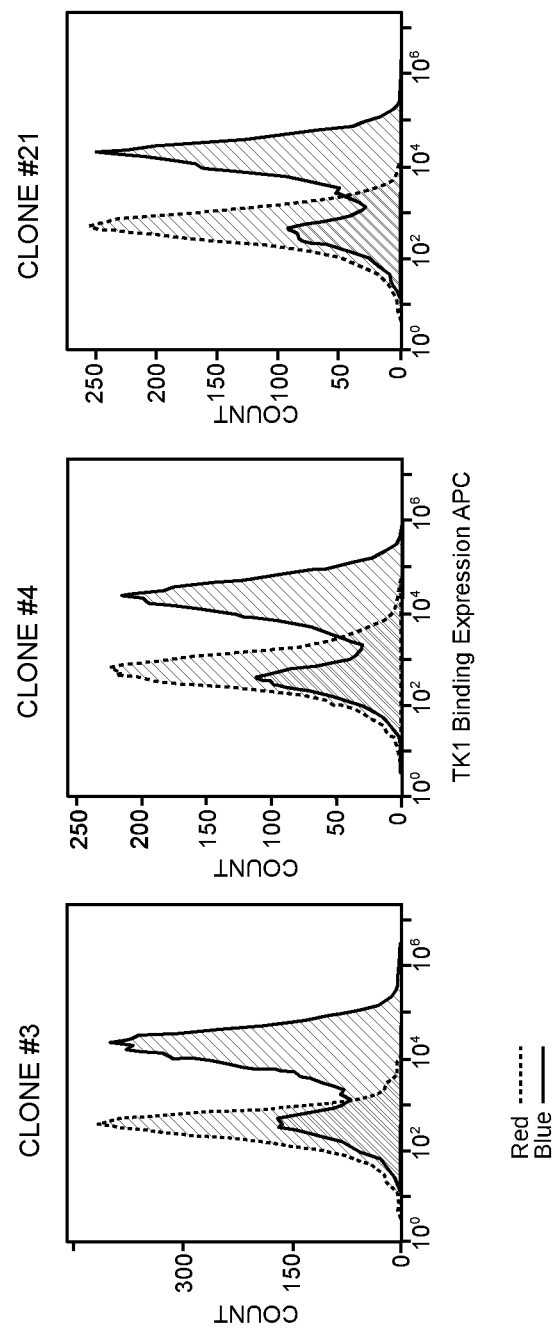
FIG. 9 is a graph illustrating HGPRT protein surface expression compared with APRT nad dCK two other salvage pathway enzymes. (b) confirms using flow cytometry the presence of HGPRT on the cell surface.

Referring to FIG. 9, $10^5$ yeast were incubated with 2.5 ug of protein of interest labeled with the fluorescent tag APC. The higher left (red) peak indicates yeast population that was not binding to the protein of interest (our negative control). The lower left (blue) peak on the left illustrates yeast not expressing their surface protein while the high (blue) peak on the right indicates binding of the expressed antibody fragment to the protein of interest.

Structural Consensus among Antibodies Defines the Antigen Binding Site. PLoS Comput Biol 8(2): e1002388. doi: 10.1371/journal.pcbi.1002388. Kunik V, Ashkenazi S, Ofran Y (2012). Paratome: An online tool for systematic identification of antigen binding regions in antibodies based on sequence or structure. Nucleic Acids Res. 2012 July; 40(Web Server issue):W521-4. doi: 10.1093/nar/gks480. Epub 2012 Jun. 6

Discovery

As aspect is the use of a CAR or BiTE produced with a scFv from a humanized or non-human mammal (such as mouse) monoclonal antibody to HPRT and TK1, that could be used with appropriate genetic engineering to manipulate macrophage lymphocytes ultimately from a patient but not limited to such, to treat a disease such as cancer. The fact that HPRT and TK1 are on the surface of cancer cells and not on the surface of any normal cell is a major part of the discovery, as this knowledge can be used to allow lymphocytes to be directed specifically to the tumor cells.

An aspect of the present system lies in the fact that using specifically generated antibodies to human HPRT or TK1 it has been discovered that HPRT and TK1 are expressed on the surface of human cancer cells and are believed not to be on the surface of normal cells and thereby can be used to target CARs and BiTEs to the tumors. While T cells have been used extensively in CAR therapy with varying results it is also proposed to use genetically modified macrophages using scFv from unique antibodies attached to a cytoplasmic domain of a Toll Like receptor such as Toll like receptor 4 to activate macrophages against tumors. This unique approach overcomes many of the inherent problems associated with the current T cell CAR technology. Utilizing the killing power of macrophages directed at specific unique targets on tumor cells allows for the enhanced response without the major drawbacks such as cytokine storm, memory activation, and on target off target problems.

An aspect is to couple the potential of a specific monoclonal antibody against a human tumor antigen to that activation receptor of patient macrophages to ensure a localized M1 response directed specifically towards the tumor. This application is to protect the technology that would allow the use of a CAR or BiTE produced with a scFv from a humanized or mouse monoclonal antibody to HPRT, TK1 or other tumor antigen, that could be used with appropriate genetic engineering to manipulate macrophages, neutrophils or other immune cells ultimately from a patient but not limited to such, to treat a disease such as cancer. The scFv from the humanized mouse monoclonal would be engineered to attach to the transmembrane and cytoplasmic domain of the TLR4, resulting in a TLR4 macrophage chimeric antigen receptor. That fact that HPRT is on the surface of cancer cells and not on the surface of any normal cell is a major part of the discovery, as this knowledge and these techniques can be used to allow the macrophages to be directed, (using the HPRT monoclonal portion) and activated (using the TLR4 cytoplasmic domain portion), specifically against the tumor cells.

It is clear that macrophages play a significant role in cancer progression, and immunotherapies involving macrophages should be included in the treatment of this disease. The polarization of macrophages towards an M1 response with minimal side effects can be a powerful therapy against solid tumors. Inflammatory signals such as LPS or TNF-α can easily polarize macrophages towards an M1 phenotype in vitro. In vivo, substances such an LPS and TNF-α exacerbate a whole-body inflammatory response involving cells in the innate and adaptive immune system, however. They can cause fever and inflammation in several tissues including the mucosal surfaces and the lungs. These inflammatory signals are highly cytotoxic as well (Apostolaki, Armaka, Victoratos, & Kollias, 2010; Kolb & Granger, 1968; Michel & Nagy, 1997). Immunotherapy requires the activation of the immune system however it is difficult to find a cytokine, chemokine, compound, or biomaterial that will not produce some side effects. Macrophages belong to the innate immune system and exhibit pro-inflammatory and anti-inflammatory properties, they are the ideal immunotherapy candidates.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

TABLE OF REFERENCES A

1. Hanahan, D., & Weinberg, R. a. (2011). Hallmarks of cancer: the next generation. *Cell, 144*(5), 646-74. http://doi.org/10.1016/j.cell.2011.02.013
2. American Cancer Society. (2015). *Cancer Facts & FIGS. 2015.*
3. Hoyert, D. L., & Xu, J. (2012). *National Vital Statistics Reports Deaths: Preliminary Data for 2011* (Vol. 61).
4. Kurahara, H., Shinchi, H., Mataki, Y., Maemura, K., Noma, H., Kubo, F., . . . Takao, S. (2011). Significance of M2-polarized tumor-associated macrophage in pancreatic cancer. *The Journal of Surgical Research, 167*(2), e211-9. http://doi.org/10.1016/j.jss.2009.05.026
5. Steidl, C., Lee, T., & Shah, S. (2010a). Tumor-associated macrophages and survival in classic Hodgkin's lymphoma. *The New England Journal of Medicine,* 875-885. Retrieved from http://www.nejm.org/doi/full/10.1056/NEJMoa0905680
6. Eiró, N., & Vizoso, F. J. (2012). Inflammation and cancer. *World Journal of Gastrointestinal Surgery, 4*(3), 62-72. http://doi.org/10.4240/wjgs.v4.i3.62
7. Kelly, P. M., Davison, R. S., Bliss, E., & McGee, J. O. (1988). Macrophages in human breast disease: a quantitative immunohistochemical study. *British Journal of Cancer, 57*(2), 174-7. Retrieved from http://www.pubmedcentral.nih.gov/articlerender.fcgi?artid=2246436&tool=pmcentrez&rendertype=abstract
8. Lewis, C., & Leek, R. (1995). Cytokine regulation of angiogenesis in breast cancer: the role of tumor-associated macrophages. *Journal of Leukocyte . . ., 57*(May), 747-751. Retrieved from http://www.jleukbio.org/content/57/5/747.short
9. Mantovani, A., Biswas, S. K., Galdiero, M. R., Sica, A., & Locati, M. (2013). Macrophage plasticity and polarization in tissue repair and remodelling. *The Journal of Pathology, 229*(2), 176-85. http://doi.org/10.1002/path.4133
10. Porta, C., Rimoldi, M., Raes, G., Brys, L., Ghezzi, P., Di Liberto, D., . . . Sica, A. (2009). Tolerance and M2 (alternative) macrophage polarization are related processes orchestrated by p50 nuclear factor kappaB. *Proceedings of the National Academy of Sciences of the United States of America, 106*(35), 14978-83. http://doi.org/10.1073/pnas.0809784106

TABLE OF REFERENCES A

11. Sica, A., & Mantovani, A. (2012). Macrophage plasticity and polarization: in vivo veritas. *The Journal of Clinical Investigation, 122*(3), 787-796. http://doi.org/10.1172/JCI59643DS1
12. Anderson, C. F., & Mosser, D. M. (2002). A novel phenotype for an activated macrophage: the type 2 activated macrophage. *Journal of Leukocyte Biology, 72*(1), 101-6. Retrieved from http://www.ncbi.nlm.nih.gov/pubmed/12101268
13. Ghassabeh, G. H., De Baetselier, P., Brys, L., Noël, W., Van Ginderachter, J. a, Meerschaut, S., . . . Raes, G. (2006). Identification of a common gene signature for type II cytokine-associated myeloid cells elicited in vivo in different pathologic conditions. *Blood, 108*(2), 575-83. http://doi.org/10.1182/blood-2005-04-1485
14. Liao, X., Sharma, N., & Kapadia, F. (2011). Krüppel-like factor 4 regulates macrophage polarization. *The Journal of Clinical Investigation, 121*(7). http/doi.org/10.1172/JCI45444DS1
15. Davis, M. J., Tsang, T. M., Qiu, Y., Dayrit, J. K., Freij, J. B., Huffnagle, G. B., & Olszewski, M. A. (2013). Macrophage M1/M2 polarization dynamically adapts to changes in cytokine microenvironments in Cryptococcus neoformans infection. *mBio, 4*(3), e00264-13. http://doi.org/10.1128/mBio.00264-13
16. Mantovani, A., Sozzani, S., Locati, M., Allavena, P., & Sica, A. (2002). Macrophage polarization: tumor-associated macrophages as a paradigm for polarized M2 mononuclear phagocytes. *Trends in Immunology, 23*(11), 549-55. Retrieved from http://www.ncbi.nlm.nih.gov/pubmed/12401408
17. Edin, S., Wikberg, M. L., Dahlin, A. M., Rutegård, J., Oberg, A., Oldenborg, P.-A., & Palmqvist, R. (2012). The distribution of macrophages with a m1 or m2 phenotype in relation to prognosis and the molecular characteristics of colorectal cancer. PloS One, 7(10), e47045. http://doi.org/10.1371/journal.pone.0047045
18. Forssell, J., Oberg, A., Henriksson, M. L., Stenling, R., Jung, A., & Palmqvist, R. (2007). High macrophage infiltration along the tumor front correlates with improved survival in colon cancer. *Clinical Cancer Research, 13*(5), 1472-9. http://doi.org/10.1158/1078-0432.CCR-06-2073
19. Guiducci, C., Vicari, A. P., Sangaletti, S., Trinchieri, G., & Colombo, M. P. (2005). Redirecting in vivo elicited tumor infiltrating macrophages and dendritic cells towards tumor rejection. *Cancer Research, 65*(8), 3437-46. http://doi.org/10.1158/0008-5472.CAN-04-4262
20. Baccala, R., Hoebe, K., Kono, D. H., Beutler, B., & Theofilopoulos, A. N. (2007). TLR-dependent and TLR-independent pathways of type I interferon induction in systemic autoimmunity. *Nature Medicine, 13*(5), 543-51. http://doi.org/10.1038/nm1590
21. Banerjee, S., Xie, N., Cui, H., Tan, Z., Yang, S., Icyuz, M., . . . Liu, G. (2013). MicroRNA let-7c regulates macrophage polarization. *Journal of Immunology (Baltimore, Md.: 1950), 190*(12), 6542-9. http://doi.org/10.4049/jimmunol.1202496
22. Murray, P. J., Allen, J. E., Biswas, S. K., Fisher, E. A., Gilroy, D. W., Goerdt, S., . . . Wynn, T. A. (2014). Macrophage Activation and Polarization: Nomenclature and Experimental Guidelines. *Immunity, 41*(1), 14-20. http://doi.org/10.1016/j.immuni.2014.06.008
23. Hao, N.-B., Lü, M.-H., Fan, Y.-H., Cao, Y.-L., Zhang, Z.-R., & Yang, S.-M. (2012). Macrophages in tumor microenvironments and the progression of tumors. *Clinical & Developmental Immunology, 2012,* 948098. http://doi.org/10.1155/2012/948098
24. Sinha, P., Clements, V. K., & Ostrand-Rosenberg, S. (2005). Reduction of myeloid-derived suppressor cells and induction of M1 macrophages facilitate the rejection of established metastatic disease. *Journal of Immunology, 174*(2), 636-45. Retrieved from http://www.ncbi.nlm.nih.gov/pubmed/15634881
25. Bingle, L., Brown, N. J., & Lewis, C. E. (2002). The role of tumour-associated macrophages in tumour progression: implications for new anticancer therapies. *The Journal of Pathology, 196*(3), 254-65. http://doi.org/10.1002/path.1027
26. Herbeuval, J.-P., Lambert, C., Sabido, O., Cottier, M., Fournel, P., Dy, M., & Genin, C. (2003). Macrophages from cancer patients: analysis of TRAIL, TRAIL receptors, and colon tumor. *Journal of the National Cancer Institute, 95*(8), 611-21. Retrieved from http://www.ncbi.nlm.nih.gov/pubmed/12697854
27. Ma, J., Liu, L., Che, G., Yu, N., Dai, F., & You, Z. (2010). The M1 form of tumor-associated macrophages in non-small cell lung cancer is positively associated with survival time. *BMC Cancer, 10,* 112. http://doi.org/10.1186/1471-2407-10-112
28. Ohri, C. M., Shikotra, A., Green, R. H., Waller, D. a, & Bradding, P. (2009). Macrophages within NSCLC tumour islets are predominantly of a cytotoxic M1 phenotype associated with extended survival. *The European Respiratory Journal, 33*(1), 118-26. http://doi.org/10.1183/09031936.00065708

TABLE OF REFERENCES A

29. Urban, J. L., Shepard, H. M., Rothstein, J. L., Sugarman, B. J., & Schreiber, H. (1986). Tumor necrosis factor: a potent effector molecule for tumor cell killing by activated macrophages. *Proceedings of the National Academy of Sciences of the United States of America, 83*(14), 5233-7. Retrieved from http://www.pubmedcentral.nih.gov/articlerender.fcgi?artid=323925&tool=pmcentrez&rendertype=abstract
30. Wong, S.-C., Puaux, A.-L., Chittezhath, M., Shalova, I., Kajiji, T. S., Wang, X., . . . Biswas, S. K. (2010). Macrophage polarization to a unique phenotype driven by B cells. *European Journal of Immunology, 40*(8), 2296-307. http://doi.org/10.1002/eji.200940288
31. Hardison, S. E., Herrera, G., Young, M. L., Hole, C. R., Wozniak, K. L., & Wormley, F. L. (2012). Protective immunity against pulmonary cryptococcosis is associated with STAT1-mediated classical macrophage activation. Journal of Immunology (*Baltimore, Md.: 1950*), *189*(8), 4060-8. http://doi.org/10.4049/jimmunol.1103455
32. Wang, Y.-C., He, F., Feng, F., Liu, X.-W., Dong, G.-Y., Qin, H.-Y., . . . Han, H. (2010). Notch signaling determines the M1 versus M2 polarization of macrophages in antitumor immune responses. *Cancer Research, 70*(12), 4840-9. http://doi.org/10.1158/0008-5472.CAN-10-0269
33. Cai, X., Yin, Y., Li, N., Zhu, D., Zhang, J., Zhang, C.-Y., & Zen, K. (2012). Re-polarization of tumor-associated macrophages to pro-inflammatory M1 macrophages by microRNA-155. *Journal of Molecular Cell Biology, 4*(5), 341-3. http://doi.org/10.1093/jmcb/mjs044
34. Wei, Y., Nazari-Jahantigh, M., Chan, L., Zhu, M., Heyll, K., Corbalan-Campos, J., . . . Schober, A. (2013). The microRNA-342-5p fosters inflammatory macrophage activation through an Akt1- and microRNA-155-dependent pathway during atherosclerosis. *Circulation, 127*(15), 1609-19. http://doi.org/10.1161/CIRCULATIONAHA.112.000736
35. Squadrito, M. L., Etzrodt, M., De Palma, M., & Pittet, M. J. (2013). MicroRNA-mediated control of macrophages and its implications for cancer. *Trends in Immunology, 34*(7), 350-9. http://doi.org/10.1016/j.it.2013.02.003
36. Biswas, S. K., Gangi, L., Paul, S., Schioppa, T., Saccani, A., Sironi, M., . . . Sica, A. (2006). A distinct and unique transcriptional program expressed by tumor-associated macrophages (defective NF-kappaB and enhanced IRF-3/STAT1 activation). *Blood, 107*(5), 2112-22. http://doi.org/10.1182/blood-2005-01-0428
37. Steidl, C., Lee, T., & Shah, S. (2010b). Tumor-associated macrophages and survival in classic Hodgkin's lymphoma. *The New England Journal of Medicine, 362*(10), 875-885. Retrieved from http://www.nejm.org/doi/full/10.1056/NEJMoa0905680
38. Lin, E. Y., Li, J.-F., Gnatovskiy, L., Deng, Y., Zhu, L., Grzesik, D. a, . . . Pollard, J. W. (2006). Macrophages regulate the angiogenic switch in a mouse model of breast cancer. *Cancer Research, 66*(23), 11238-46. http://doi.org/10.1158/0008-5472.CAN-06-1278
39. Hagemann, T., Wilson, J., Burke, F., Kulbe, H., Li, N. F., Pluddemann, A., . . . Balkwill, F. R. (2006). Ovarian cancer cells polarize macrophages toward a tumor-associated phenotype. *The Journal of Immunology, 176*(8), 5023-32. Retrieved from http://www.ncbi.nlm.nih.gov/pubmed/16585599
40. Hagemann, T., Lawrence, T., McNeish, I., Charles, K. a, Kulbe, H., Thompson, R. G., . . . Balkwill, F. R. (2008). "Re-educating" tumor-associated macrophages by targeting NF-kappaB. *The Journal of Experimental Medicine, 205*(6), 1261-8. http://doi.org/10.1084/jem.20080108
41. Mandal, P., Pratt, B. T., Barnes, M., McMullen, M. R., & Nagy, L. E. (2011). Molecular mechanism for adiponectin-dependent M2 macrophage polarization: link between the metabolic and innate immune activity of full-length adiponectin. *The Journal of Biological Chemistry, 286*(15), 13460-9. http://doi.org/10.1074/jbc.M110.204644
42. Mantovani, A., Allavena, P., Sica, A., & Balkwill, F. (2008). Cancer-related inflammation. *Nature, 454*(7203), 436-44. http://doi.org/10.1038/nature07205
43. Cortez-Retamozo, V., Etzrodt, M., Newton, A., Rauch, P. J., Chudnovskiy, A., Berger, C., . . . Pittet, M. J. (2012). Origins of tumor-associated macrophages and neutrophils. *Proceedings of the National Academy of Sciences of the United States of America, 109*(7), 2491-6. http://doi.org/10.1073/pnas.1113744109
44. Hercus, T. R., Thomas, D., Guthridge, M. A., Ekert, P. G., King-Scott, J., Parker, M. W., & Lopez, A. F. (2009). The granulocyte-macrophage colony-stimulating factor receptor: linking its structure to cell signaling and its role in disease. *Blood, 114*(7), 1289-98. http://doi.org/10.1182/blood-2008-12-164004

-continued

TABLE OF REFERENCES A

45. Smith, H. O., Stephens, N. D., Qualls, C. R., Fligelman, T., Wang, T., Lin, C.-Y., . . . Pollard, J. W. (2013). The clinical significance of inflammatory cytokines in primary cell culture in endometrial carcinoma. *Molecular Oncology, 7*(1), 41-54. http://doi.org/10.1016/j.molonc.2012.07.002
46. West, R. B., Rubin, B. P., Miller, M. A., Subramanian, S., Kaygusuz, G., Montgomery, K., . . . van de Rijn, M. (2006). A landscape effect in tenosynovial giant-cell tumor from activation of CSF1 expression by a translocation in a minority of tumor cells. *Proceedings of the National Academy of Sciences of the United States of America, 103*(3), 690-5. http://doi.org/10.1073/pnas.0507321103
47. Lin, E. Y., & Pollard, J. W. (2007). Tumor-associated macrophages press the angiogenic switch in breast cancer. *Cancer Research, 67*(11), 5064-6. http://doi.org/10.1158/0008-5472.CAN-07-0912
48. Dalton, H. J., Armaiz-Pena, G. N., Gonzalez-Villasana, V., Lopez-Berestein, G., Bar-Eli, M., & Sood, A. K. (2014). Monocyte subpopulations in angiogenesis. *Cancer Research, 74*(5), 1287-93. http://doi.org/10.1158/0008-5472.CAN-13-2825
49. Saccani, A., Schioppa, T., Porta, C., Biswas, S. K., Nebuloni, M., Vago, L., . . . Sica, A. (2006). p50 nuclear factor-kappaB overexpression in tumor-associated macrophages inhibits M1 inflammatory responses and antitumor resistance. *Cancer Research, 66*(23), 11432-40. http://doi.org/10.1158/0008-5472.CAN-06-1867
50. Gazzaniga, S., Bravo, A. I., Guglielmotti, A., van Rooijen, N., Maschi, F., Vecchi, A., . . . Wainstok, R. (2007). Targeting tumor-associated macrophages and inhibition of MCP-1 reduce angiogenesis and tumor growth in a human melanoma xenograft. *The Journal of Investigative Dermatology, 127*(8), 2031-41. http://doi.org/10.1038/sj.jid.5700827
51. Luo, Y., Zhou, H., & Krueger, J. (2006). Targeting tumor-associated macrophages as a novel strategy against breast cancer. *Journal of Clinical Investigation, 116*(8), 2132-2141. http://doi.org/10.1172/JCI27648.2132
52. Zeisberger, S. M., Odermatt, B., Marty, C., Zehnder-Fjällman, a H. M., Ballmer-Hofer, K., & Schwendener, R. a. (2006). Clodronate-liposome-mediated depletion of tumour-associated macrophages: a new and highly effective antiangiogenic therapy approach. *British Journal of Cancer, 95*(3), 272-81. http://doi.org/10.1038/sj.bjc.6603240
53. Bettencourt-Dias, M., Giet, R., Sinka, R., Mazumdar, a, Lock, W. G., Balloux, F., . . . Glover, D. M. (2004). Genome-wide survey of protein kinases required for cell cycle progression. *Nature, 432*(7020), 980-7. http://doi.org/10.1038/nature03160
54. Geschwind, J. H., Vali, M., & Wahl, R. (2006). Effects of 3 bromopyruvate (hexokinase 2 inhibitor) on glucose uptake in lewis rats using 2-(F-18) fluoro-2-deoxy-d-glucose. In *2006 Gastrointestinal Cancers Symposium* (pp. 12-14).
55. Wolf, A., Agnihotri, S., Micallef, J., Mukherjee, J., Sabha, N., Cairns, R., . . . Guha, A. (2011). Hexokinase 2 is a key mediator of aerobic glycolysis and promotes tumor growth in human glioblastoma multiforme. *The Journal of Experimental Medicine, 208*(2), 313-26. http://doi.org/10.1084/jem.20101470
56. Blagih, J., & Jones, R. G. (2012). Polarizing macrophages through reprogramming of glucose metabolism. *Cell Metabolism, 15*(6), 793-5. http://doi.org/10.1016/j.cmet.2012.05.008
57. Haschemi, A., Kosma, P., Gille, L., Evans, C. R., Burant, C. F., Starkl, P., . . . Wagner, O. (2012). The sedoheptulose kinase CARKL directs macrophage polarization through control of glucose metabolism. *Cell Metabolism, 15*(6), 813-26. http://doi.org/10.1016/j.cmet.2012.04.023
58. Arranz, A., Doxaki, C., Vergadi, E., Martinez de la Torre, Y., Vaporidi, K., Lagoudaki, E. D., . . . Tsatsanis, C. (2012). Akt1 and Akt2 protein kinases differentially contribute to macrophage polarization. *Proceedings of the National Academy of Sciences of the United States of America, 109*(24), 9517-22. http://doi.org/10.1073/pnas.1119038109
59. Jones, R. G., & Thompson, C. B. (2007). Revving the engine: signal transduction fuels T cell activation. *Immunity, 27*(2), 173-8. http://doi.org/10.1016/j.immuni.2007.07.008
60. Shu, C. J., Guo, S., Kim, Y. J., Shelly, S. M., Nijagal, A., Ray, P., . . . Witte, O. N. (2005). Visualization of a primary anti-tumor immune response by positron emission tomography. *Proceedings of the National Academy of Sciences of the United States of America, 102*(48), 17412-7. http://doi.org/10.1073/pnas.0508698102
61. Van Ginderachter, J. A., Movahedi, K., Hassanzadeh Ghassabeh, G., Meerschaut, S., Beschin, A., Raes, G., & De Baetselier, P. (2006). Classical and alternative activation of mononuclear phagocytes: Picking the best of both worlds for tumor promotion. *Immunobiology, 211*(6), 487-501. Retrieved from http://www.sciencedirect.com/science/article/pii/S0171298506000829

| TABLE OF REFERENCES A |
|---|
| 62. Mills, C. D., Shearer, J., Evans, R., & Caldwell, M. D. (1992). Macrophage arginine metabolism and the inhibition or stimulation of cancer. *Journal of Immunology (Baltimore, Md.: 1950), 149*(8), 2709-14. Retrieved from http://www.ncbi.nlm.nih.gov/pubmed/1401910 |
| 63. Ji, Y., Sun, S., Xu, A., Bhargava, P., Yang, L., Lam, K. S. L., . . . Qi, L. (2012). Activation of natural killer T cells promotes M2 Macrophage polarization in adipose tissue and improves systemic glucose tolerance via interleukin-4 (IL-4)/STAT6 protein signaling axis in obesity. *The Journal of Biological Chemistry, 287*(17), 13561-71. http://doi.org/10.1074/jbc.M112.350066 |
| 64. Andreesen, R., Scheibenbogen, C., & Brugger, W. (1990). Adoptive transfer of tumor cytotoxic macrophages generated in vitro from circulating blood monocytes: a new approach to cancer immunotherapy. *Cancer Research,* 7450-7456. Retrieved from http://cancerres.aacrjournals.org/content/50/23/7450.short |
| 65. Korbelik, M., Naraparaju, V. R., & Yamamoto, N. (1997). Macrophage-directed immunotherapy as adjuvant to photodynamic therapy of cancer. *British Journal of Cancer, 75*(2), 202-7. Retrieved from http://www.pubmedcentral.nih.gov/articlerender.fcgi?artid=2063270&tool=pmcentrez&rendertype=abstract |
| 66. Ellem, K. A. O., Rourke, M. G. E. O., Johnson, G. R., Parry, G., Misko, I. S., Schmidt, C. W., . . . Mulligan, R. C. (1997). A case report: immune responses and clinical course of the first human use of granulocyte/macrophage-colony-stimulating-factor-transduced autologous melanoma. *Cancer Immunology, Immunotherapy,* 10-20. Retrieved from http://www.springerlink.com/index/JQ4EB21E4C7ADMT7.pdf |
| 67. Gast, G. de, & Klümpen, H. (2000). immunotherapy with subcutaneous granulocyte macrophage colony-stimulating factor, low-dose interleukin 2, and interferon α in progressive metastatic melanoma. *Clinical Cancer Research.* Retrieved from http://clincancerres.aacrjournals.org/content/6/4/1267.short |
| 68. Hill, H., Jr, T. C., & Sabel, M. (2002). Immunotherapy with Interleukin 12 and Granulocyte-Macrophage Colony-stimulating Factor-encapsulated Microspheres Coinduction of Innate and Adaptive Antitumor. *Cancer Research.* Retrieved from http://cancerres.aacrjournals.org/content/62/24/7254.short |
| 69. Lokshin, A., Mayotte, J., & Levitt, M. (1995). Mechanism of Interferon Beta-Induced Squamous Differentiation and Programmed Cell Death in Human Non-Small-Cell Lung Cancer Cell Lines. *Journal of the National Cancer Institute, 87,* 206-212. Retrieved from http://jnci.oxfordjournals.org/content/87/3/206.short |
| 70. Johns, T., & Mackay, I. (1992). Antiproliferative potencies of interferons on melanoma cell lines and xenografts: higher efficacy of interferon $\beta^2$. *Journal of the National Cancer Institute,* (type II), 1185-1190. Retrieved from http://jnci.oxfordjournals.org/content/84/15/1185 |
| 71. Qin, X.-Q., Runkel, L., Deck, C., DeDios, C., & Barsoum, J. (1997). Interferon-beta induces S phase accumulation selectively in human transformed cells. *Journal of Interferon & Cytokine Research, 17*(6), 355-367. http://doi.org/10.1089/jir.1997.17.355 |
| 72. Zhang, F., Lu, W., & Dong, Z. (2002). Tumor-infiltrating macrophages are involved in suppressing growth and metastasis of human prostate cancer cells by INF-β gene therapy in nude mice. *Clinical Cancer Research,* 2942-2951. Retrieved from http://clincancerres.aacrjournals.org/content/8/9/2942.short |
| 73. Simpson, K. D., Templeton, D. J., & Cross, J. V. (2012). Macrophage Migration Inhibitory Factor Promotes Tumor Growth and Metastasis by Inducing Myeloid-Derived Suppressor Cells in the Tumor Microenvironment. *The Journal of Immunology.* http://doi.org/10.4049/jimmunol.1201161 |
| 74. Sanford, D. E., Belt, B. A., Panni, R. Z., Mayer, A., Deshpande, A. D., Carpenter, D., . . . Linehan, D. C. (2013). Inflammatory monocyte mobilization decreases patient survival in pancreatic cancer: a role for targeting the CCL2/CCR2 axis. *Clinical Cancer Research: An Official Journal of the American Association for Cancer Research, 19*(13), 3404-15. http://doi.org/10.1158/1078-0432.CCR-13-0525 |
| 75. Schmall, A., Al-Tamari, H. M., Herold, S., Kampschulte, M., Weigert, A., Wietelmann, A., . . . Savai, R. (2014). Macrophage and Cancer Cell Crosstalk via CCR2 and CX3CR1 is a Fundamental Mechanism Driving Lung Cancer. *American Journal of Respiratory and Critical Care Medicine.* http://doi.org/10.1164/rccm.201406-1137OC |
| 76. Kimura, Y. N., Watari, K., Fotovati, A., Hosoi, F., Yasumoto, K., Izumi, H., . . . Ono, M. (2007). Inflammatory stimuli from macrophages and cancer cells synergistically promote tumor growth and angiogenesis. *Cancer Science, 98*(12), 2009-18. http://doi.org/10.1111/j.1349-7006.2007.00633.x |

TABLE OF REFERENCES A

77. Chen, H., Li, P., Yin, Y., Cai, X., Huang, Z., Chen, J., . . . Zhang, J. (2010). The promotion of type 1 T helper cell responses to cationic polymers in vivo via toll-like receptor-4 mediated IL-12 secretion. *Biomaterials, 31*(32), 8172-80. http://doi.org/10.1016/j.biomaterials.2010.07.056
78. Rogers, T. L., & Holen, I. (2011). Tumour macrophages as potential targets of bisphosphonates. *Journal of Translational Medicine, 9*(1), 177. http://doi.org/10.1186/1479-5876-9-177
79. Junankar, S., Shay, G., Jurczyluk, J., Ali, N., Down, J., Pocock, N., . . . Rogers, M. J. (2015). Real-time intravital imaging establishes tumor-associated macrophages as the extraskeletal target of bisphosphonate action in cancer. *Cancer Discovery, 5*(1), 35-42. http://doi.org/10.1158/2159-8290.CD-14-0621
80. Huang, Z., Yang, Y., Jiang, Y., Shao, J., Sun, X., Chen, J., . . . Zhang, J. (2013). Anti-tumor immune responses of tumor-associated macrophages via toll-like receptor 4 triggered by cationic polymers. *Biomaterials, 34*(3), 746-55. http://doi.org/10.1016/j.biomaterials.2012.09.062
81. Q. He, T. Fornander, H. Johansson et al., "Thymidine kinase 1 in serum predicts increased risk of distant or loco-regional recurrence following surgery in patients with early breast cancer," Anticancer Research, vol. 26, no. 6, pp. 4753-4759, 2006.
82. K. L. O'Neill, M. Hoper, and G. W. Odling-Smee, "Can thymidine kinase levels in breast tumors predict disease recurrence?" Journal of the National Cancer Institute, vol. 84, no. 23, pp. 1825-1828, 1992.
83. Apostolaki, M., Armaka, M., Victoratos, P., & Kollias, G. (2010). Cellular Mechanisms of TNF Function in Models of Inflammation and Autoimmunity - Karger Publishers. Retrieved Sep. 12, 2013, from http://www.karger.com/Article/Abstract/289195
84. Kolb, W., & Granger, G. (1968). Lymphocyte in vitro cytotoxicity: characterization of human lymphotoxin. *Proceedings of the National Academy of Sciences of the United States of America,* 1250-1255. Retrieved from http://www.ncbi.nlm.nih.gov/pmc/articles/PMC225248/
85. Michel, O., & Nagy, A. (1997). Dose-response relationship to inhaled endotoxin in normal subjects. *American Journal of Respiratory and Critical Care Medicine, 156*(4 Pt 1), 1157-64. Retrieved from http://www.atsjournals.org/doi/abs/10.1164/ajrccm.156.4.97-02002

TABLE OF REFERENCES B

American Cancer Society, Cancer Facts and FIGS. 2015.
Schreiber H. Tumor-specific immune responses. SeminImmunol 2008; 20: 265-6; PMID: 18977672; http://dx.doi.org/10.1016/j.smim.2008.10.001.
Stone, J. D. Aggen, D. H., Scheitinger, A, Schreiber, H, and Kranz, D. M. 2012 A sensitivity scale for targeting T cells with Chimeric Antigen Receptors (CARs) and Bispecific T-cell engagers (BiTEs) Onclommunology 1: 6, 863-873
Schreiber H. Cancer Immunology. Philadelphia, PA: Lippincott-Williams & Wilkins 2012.
Karyampudi L, Knutson KL. Antibodies in cancer immunotherapy. Cancer Biomark 2010; 6: 291-305; PMID: 20938089.
Grillo-L. pez AJ, White CA, Varns C, Shen D, Wei A, McClure A, et al. Overview of the clinical development of rituximab: first monoclonal antibody approved for the treatment of lymphoma. Semin Oncol 1999; 26: 66-73; PMID: 10561020.
Goldenberg MM. Trastuzumab, a recombinant DNA derived humanized monoclonal antibody, a novel agent for the treatment of metastatic breast cancer. Clin Ther 1999; 21: 309-18; PMID: 10211534; http://dx.doi.org/10.1016/S0149-2918(00)88288-0.
Seliger B, Cabrera T, Garrido F, Ferrone S. HLA class I antigen abnormalities and immune escape by malignant cells. Semin Cancer Biol 2002; 12: 3-13; PMID: 11926409; http://dx.doi.org/10.1006/scbi.2001.0404.
Garrido F, Cabrera T, Concha A, Glew S, Ruiz-Cabello F, Stern PL. Natural history of HLA expression during tumour development. Immunol Today 1993; 14: 491 9; PMID: 8274189; http://dx.doi.org/10.1016/0167-5699(93)90264-L.
Meidenbauer N, Zippelius A, Pittet MJ, Laumer M, Vogl S, Heymann J, et al. High frequency of functionally active Melan-a-specific T cells in a patient with progressive immunoproteasome-deficient melanoma. Cancer Res 2004; 64: 6319-26; PMID: 15342421; http://dx.doi.org/10.1158/0008-5472.CAN-04-1341.
Yu Z, Theoret MR, Touloukian CE, Surman DR, Garman SC, Feigenbaum L, et al. Poor immunogenicity of a self/tumor antigen derives from peptide-MHCI instability and is independent of tolerance. J Clin Invest 2004; 114: 551-9; PMID: 15314692.

TABLE OF REFERENCES B

Alegre. M, Robison, R. A. and O'Neill, K. L. Thymidine Kinase 1: A Universal Marker for Cancer. 2013 Cancer and Clinical Oncology 2013 vol 2: No 1; p 159-167.

O'Neill, K. L., Buckwalter, M. R., & Murray, B. K. (2001). Thymidine kinase: diagnostic and prognostic potential. Expert Rev Mol Diagn, 1 (4), 428-433. http://dx.doi.org/10.1586/14737159.1.4.428

American Cancer Society. (2015). Cancer Facts & FIGS. 2015.

Anderson, C. F., & Mosser, D. M. (2002). A novel phenotype for an activated macrophage: the type 2 activated macrophage. Journal of Leukocyte Biology, 72(1), 101-6. Retrieved from http://www.ncbi.nlm.nih.gov/pubmed/12101268

Andreesen, R., Scheibenbogen, C., & Brugger, W. (1990). Adoptive transfer of tumor cytotoxic macrophages generated in vitro from circulating blood monocytes: a new approach to cancer immunotherapy. Cancer Research, 7450-7456. Retrieved from http://cancerres.aacrjournals.org/content/50/23/7450.short Apostolaki, M., Armaka, M., Victoratos, P., & Kollias, G. (2010). Cellular Mechanisms of TNF Function in Models of Inflammation and Autoimmunity - Karger Publishers. Retrieved Sep. 12, 2013, from http://www.karger.com/Article/Abstract/289195

Arranz, A., Doxaki, C., Vergadi, E., Martinez de la Torre, Y., Vaporidi, K., Lagoudaki, E. D., . . . Tsatsanis, C. (2012). Akt1 and Akt2 protein kinases differentially contribute to macrophage polarization. Proceedings of the National Academy of Sciences of the United States of America, 109(24), 9517-22. http://doi.org/10.1073/pnas.1119038109

Baccala, R., Hoebe, K., Kono, D. H., Beutler, B., & Theofilopoulos, A. N. (2007). TLR-dependent and TLR-independent pathways of type I interferon induction in systemic autoimmunity. Nature Medicine, 13(5), 543-51. http://doi.org/10.1038/nm1590

Banerjee, S., Xie, N., Cui, H., Tan, Z., Yang, S., Icyuz, M., . . . Liu, G. (2013). MicroRNA let-7c regulates macrophage polarization. Journal of Immunology (Baltimore, Md.: 1950), 190(12), 6542-9. http://doi.org/10.4049/jimmunol.1202496

Barros, M. H. M., Hauck, F., Dreyer, J. H., Kempkes, B., & Niedobitek, G. (2013). Macrophage Polarisation: an Immunohistochemical Approach for Identifying M1 and M2 Macrophages. PloS One, 8(11), e80908. http://doi.org/10.1371/journal.pone.0080908

Bettencourt-Dias, M., Giet, R., Sinka, R., Mazumdar, a, Lock, W. G., Balloux, F., . . . Glover, D. M. (2004). Genome-wide survey of protein kinases required for cell cycle progression. Nature, 432(7020), 980-7. http://doi.org/10.1038/nature03160

Bingle, L., Brown, N. J., & Lewis, C. E. (2002). The role of tumour-associated macrophages in tumour progression: implications for new anticancer therapies. The Journal of Pathology, 196(3), 254-65. http://doi.org/10.1002/path.1027

Biswas, S. K., Gangi, L., Paul, S., Schioppa, T., Saccani, A., Sironi, M., . . . Sica, A. (2006). A distinct and unique transcriptional program expressed by tumor-associated macrophages (defective NF-kappaB and enhanced IRF-3/STAT1 activation). Blood, 107(5), 2112-22. http://doi.org/10.1182/blood-2005-01-0428

Blagih, J., & Jones, R. G. (2012). Polarizing macrophages through reprogramming of glucose metabolism. Cell Metabolism, 15(6), 793-5. http://doi.org/10.1016/j.cmet.2012.05.008

Cai, X., Yin, Y., Li, N., Zhu, D., Zhang, J., Zhang, C.-Y., & Zen, K. (2012). Re-polarization of tumor-associated macrophages to pro-inflammatory M1 macrophages by microRNA-155. Journal of Molecular Cell Biology, 4(5), 341-3. http://doi.org/10.1093/jmcb/mjs044

Chen, H., Li, P., Yin, Y., Cai, X., Huang, Z., Chen, J., . . . Zhang, J. (2010). The promotion of type 1 T helper cell responses to cationic polymers in vivo via toll-like receptor-4 mediated IL-12 secretion. Biomaterials, 31(32), 8172-80. http://doi.org/10.1016/j.biomaterials.2010.07.056

Cortez-Retamozo, V., Etzrodt, M., Newton, A., Rauch, P. J., Chudnovskiy, A., Berger, C., . . . Pittet, M. J. (2012). Origins of tumor-associated macrophages and neutrophils. Proceedings of the National Academy of Sciences of the United States of America, 109(7), 2491-6. http://doi.org/10.1073/pnas.1113744109

Dalton, H. J., Armaiz-Pena, G. N., Gonzalez-Villasana, V., Lopez-Berestein, G., Bar-Eli, M., & Sood, A. K. (2014). Monocyte subpopulations in angiogenesis. Cancer Research, 74(5), 1287-93. http://doi.org/10.1158/0008-5472.CAN-13-2825

Davis, M. J., Tsang, T. M., Qiu, Y., Dayrit, J. K., Freij, J. B., Huffnagle, G. B., & Olszewski, M. A. (2013). Macrophage M1/M2 polarization dynamically adapts to changes in cytokine microenvironments in Cryptococcus neoformans infection. mBio, 4(3), e00264-13. http://doi.org/10.1128/mBio.00264-13

Edin, S., Wikberg, M. L., Dahlin, A. M., Rutegard, J., Oberg, A., Oldenborg, P.-A., & Palmqvist, R. (2012). The distribution of macrophages with a m1 or m2 phenotype in relation to prognosis and the molecular characteristics of colorectal cancer. PloS One, 7(10), e47045.

TABLE OF REFERENCES B http://doi.org/10.1371/journal.pone.0047045
Eiró, N., & Vizoso, F. J. (2012). Inflammation and cancer. World Journal of Gastrointestinal Surgery, 4(3), 62-72. http://doi.org/10.4240/wjgs.v4.i3.62
Ellem, K. A. O., Rourke, M. G. E. O., Johnson, G. R., Parry, G., Misko, I. S., Schmidt, C. W., . . . Mulligan, R. C. (1997). A case report: immune responses and clinical course of the first human use of granulocyte/macrophage-colony-stimulating-factor-transduced autologous melanoma. Cancer Immunology, Immunotherapy, 10-20. Retrieved from http://www.springerlink.com/index/JQ4EB21E4C7ADMT7.pdf
Forssell, J., Oberg, A., Henriksson, M. L., Stenling, R., Jung, A., & Palmqvist, R. (2007). High macrophage infiltration along the tumor front correlates with improved survival in colon cancer. Clinical Cancer Research, 13(5), 1472-9. http://doi.org/10.1158/1078-0432.CCR-06-2073
Gast, G. de, & Klümpen, H. (2000). immunotherapy with subcutaneous granulocyte macrophage colony-stimulating factor, low-dose interleukin 2, and interferon Î± in progressive metastatic melanoma. Clinical Cancer Research. Retrieved from http://clincancerres.aacrjournals.org/content/6/4/1267.short
Gazzaniga, S., Bravo, A. I., Guglielmotti, A., van Rooijen, N., Maschi, F., Vecchi, A., . . . Wainstok, R. (2007). Targeting tumor-associated macrophages and inhibition of MCP-1 reduce angiogenesis and tumor growth in a human melanoma xenograft. The Journal of Investigative Dermatology, 127(8), 2031-41. http://doi.org/10.1038/sj.jid.5700827
Geschwind, J. H., Vali, M., & Wahl, R. (2006). Effects of 3¬ bromopyruvate (hexokinase 2 inhibitor) on glucose uptake in lewis rats using 2-(F-18) fluoro-2-deoxy-d-glucose. In 2006 Gastrointestinal Cancers Symposium (pp. 12-14).
Ghassabeh, G. H., De Baetselier, P., Brys, L., Noël, W., Van Ginderachter, J. a, Meerschaut, S., . . . Raes, G. (2006). Identification of a common gene signature for type II cytokine-associated myeloid cells elicited in vivo in different pathologic conditions. Blood, 108(2), 575-83. http://doi.org/10.1182/blood-2005-04-1485
Guiducci, C., Vicari, A. P., Sangaletti, S., Trinchieri, G., & Colombo, M. P. (2005). Redirecting in vivo elicited tumor infiltrating macrophages and dendritic cells towards tumor rejection. Cancer Research, 65(8), 3437-46. http://doi.org/10.1158/0008-5472.CAN-04-4262
Hagemann, T., Lawrence, T., McNeish, I., Charles, K. a, Kulbe, H., Thompson, R. G., . . . Balkwill, F. R. (2008). "Re-educating" tumor-associated macrophages by targeting NF-kappaB. The Journal of Experimental Medicine, 205(6), 1261-8. http://doi.org/10.1084/jem.20080108
Hagemann, T., Wilson, J., Burke, F., Kulbe, H., Li, N. F., Pluddemann, A., . . . Balkwill, F. R. (2006). Ovarian cancer cells polarize macrophages toward a tumor-associated phenotype. The Journal of Immunology, 176(8), 5023-32. Retrieved from http://www.ncbi.nlm.nih.gov/pubmed/16585599
Hanahan, D., & Weinberg, R. a. (2011). Hallmarks of cancer: the next generation. Cell, 144(5), 646-74. http://doi.org/10.1016/j.cell.2011.02.013
Hao, N.-B., Lü, M.-H., Fan, Y.-H., Cao, Y.-L., Zhang, Z.-R., & Yang, S.-M. (2012). Macrophages in tumor microenvironments and the progression of tumors. Clinical & Developmental Immunology, 2012, 948098. http://doi.org/10.1155/2012/948098
Hardison, S. E., Herrera, G., Young, M. L., Hole, C. R., Wozniak, K. L., & Wormley, F. L. (2012). Protective immunity against pulmonary cryptococcosis is associated with STAT1-mediated classical macrophage activation. Journal of Immunology (Baltimore, Md.: 1950), 189(8), 4060-8. http://doi.org/10.4049/jimmunol.1103455
Haschemi, A., Kosma, P., Gille, L., Evans, C. R., Burant, C. F., Starkl, P., . . . Wagner, O. (2012). The sedoheptulose kinase CARKL directs macrophage polarization through control of glucose metabolism. Cell Metabolism, 15(6), 813-26. http://doi.org/10.1016/j.cmet.2012.04.023
Herbeuval, J.-P., Lambert, C., Sabido, O., Cottier, M., Fournel, P., Dy, M., & Genin, C. (2003). Macrophages from cancer patients: analysis of TRAIL, TRAIL receptors, and colon tumor cell apoptosis. Journal of the National Cancer Institute, 95(8), 611-21. Retrieved from http://www.ncbi.nlm.nih.gov/pubmed/12697854
Hercus, T. R., Thomas, D., Guthridge, M. A., Ekert, P. G., King-Scott, J., Parker, M. W., & Lopez, A. F. (2009). The granulocyte-macrophage colony-stimulating factor receptor: linking its structure to cell signaling and its role in disease. Blood, 114(7), 1289-98. http://doi.org/10.1182/blood-2008-12-164004
Hill, H., Jr, T. C., & Sabel, M. (2002). Immunotherapy with Interleukin 12 and Granulocyte-Macrophage Colony-stimulating Factor-encapsulated Microspheres Coinduction of Innate and Adaptive Antitumor. Cancer Research. Retrieved from http://cancerres.aacrjournals.org/content/62/24/7254.short
Hoyert, D. L., & Xu, J. (2012). National Vital Statistics Reports Deaths: Preliminary Data for 2011 (Vol. 61).
Hu, Y., Zhang, H., Lu, Y., Bai, H., Xu, Y., Zhu, X., . . . Chen, Q. (2011). Class A scavenger receptor attenuates myocardial infarction-induced cardiomyocyte necrosis through suppressing M1 macrophage subset polarization. Basic Research in Cardiology, 106(6), 1311-28. http://doi.org/10.1007/500395-011-0204-x

TABLE OF REFERENCES B

Huang, Z., Yang, Y., Jiang, Y., Shao, J., Sun, X., Chen, J., . . . Zhang, J. (2013). Anti-tumor immune responses of tumor-associated macrophages via toll-like receptor 4 triggered by cationic polymers. Biomaterials, 34(3), 746-55. http://doi.org/10.1016/j.biomaterials.2012.09.062

Jaffee, E., & Hruban, R. (2001). Novel allogeneic granulocyte-macrophage colony-stimulating factor-secreting tumor vaccine for pancreatic cancer: a phase I trial of safety and immune activation. Journal of Clinical . . . , 19(1), 145-156.

Ji, Y., Sun, S., Xu, A., Bhargava, P., Yang, L., Lam, K. S. L., . . . Qi, L. (2012). Activation of natural killer T cells promotes M2 Macrophage polarization in adipose tissue and improves systemic glucose tolerance via interleukin-4 (IL-4)/STAT6 protein signaling axis in obesity. The Journal of Biological Chemistry, 287(17), 13561-71. http://doi.org/10.1074/jbc.M112.350066

Johns, T., & Mackay, I. (1992). Antiproliferative potencies of interferons on melanoma cell lines and xenografts: higher efficacy of interferon 12. Journal of the National Cancer Institute, (type II), 1185-1190. Retrieved from http://jnci.oxfordjournals.org/content/84/15/1185

Jones, R. G., & Thompson, C. B. (2007). Revving the engine: signal transduction fuels T cell activation. Immunity, 27(2), 173-8. http://doi.org/10.1016/j.immuni.2007.07.008

Junankar, S., Shay, G., Jurczyluk, J., Ali, N., Down, J., Pocock, N., . . . Rogers, M. J. (2015). Real-time intravital imaging establishes tumor-associated macrophages as the extraskeletal target of bisphosphonate action in cancer. Cancer Discovery, 5(1), 35-42. http://doi.org/10.1158/2159-8290.CD-14-0621

Kelly, P. M., Davison, R. S., Bliss, E., & McGee, J. O. (1988). Macrophages in human breast disease: a quantitative immunohistochemical study. British Journal of Cancer, 57(2), 174-7. Retrieved from http://www.pubmedcentral.nih.gov/articlerender.fcgi?artid=2246436&tool=pmcentrez&rendertype=abstract Kimura, Y. N., Watari, K., Fotovati, A., Hosoi, F., Yasumoto, K., Izumi, H., . . . Ono, M. (2007). Inflammatory stimuli from macrophages and cancer cells synergistically promote tumor growth and angiogenesis. Cancer Science, 98(12), 2009-18. http://doi.org/10.1111/j.1349-7006.2007.00633.x Kolb, W., & Granger, G. (1968). Lymphocyte in vitro cytotoxicity: characterization of human lymphotoxin. Proceedings of the National Academy of Sciences of the United States of America, 1250-1255. Retrieved from http://www.ncbi.nlm.nih.gov/pmc/articles/PMC225248/

Korbelik, M., Naraparaju, V. R., & Yamamoto, N. (1997). Macrophage-directed immunotherapy as adjuvant to photodynamic therapy of cancer. British Journal of Cancer, 75(2), 202-7. Retrieved from http://www.pubmedcentral.nih.gov/articlerender.fcgi?artid=2063270&tool=pmcentrez&rendertype=abstract Kurahara, H., Shinchi, H., Mataki, Y., Maemura, K., Noma, H., Kubo, F., . . . Takao, S. (2011). Significance of M2-polarized tumor-associated macrophage in pancreatic cancer. The Journal of Surgical Research, 167(2), e211-9. http://doi.org/10.1016/j.jss.2009.05.026

Lawrence, T., & Natoli, G. (2011). Transcriptional regulation of macrophage polarization: enabling diversity with identity. Nature Reviews. Immunology, 11(11), 750-61. http://doi.org/10.1038/nri3088

Lewis, C., & Leek, R. (1995). Cytokine regulation of angiogenesis in breast cancer: the role of tumor-associated macrophages. Journal of Leukocyte . . . , 57(May), 747-751. Retrieved from http://www.jleukbio.org/content/57/5/747.short Liao, X., Sharma, N., & Kapadia, F. (2011). Kruppel-like factor 4 regulates macrophage polarization. The Journal of Clinical Investigation, 121(7). http://doi.org/10.1172/JCI45444DS1

Lin, E. Y., Li, J.-F., Gnatovskiy, L., Deng, Y., Zhu, L., Grzesik, D. a, . . . Pollard, J. W. (2006). Macrophages regulate the angiogenic switch in a mouse model of breast cancer. Cancer Research, 66(23), 11238-46. http://doi.org/10.1158/0008-5472. CAN-06-1278

Lin, E. Y., & Pollard, J. W. (2007). Tumor-associated macrophages press the angiogenic switch in breast cancer. Cancer Research, 67(11), 5064-6. http://doi.org/10.1158/0008-5472.CAN-07-0912

Lodish, H. F., Zhou, B., Liu, G., & Chen, C.-Z. (2008). Micromanagement of the immune system by microRNAs. Nature Reviews. Immunology, 8(2), 120-30. http://doi.org/10.1038/nri2252

Lokshin, A., Mayotte, J., & Levitt, M. (1995). Mechanism of Interferon Beta-Induced Squamous Differentiation and Programmed Cell Death in Human Non-Small-Cell Lung Cancer Cell Lines. Journal of the National Cancer Institute, 87, 206-212. Retrieved from http://jnci.oxfordjournals.org/content/87/3/206.short Luo, Y., Zhou, H., & Krueger, J. (2006). Targeting tumor-associated macrophages as a novel strategy against breast cancer. Journal of Clinical Investigation, 116(8), 2132-2141. http://doi.org/10.1172/JCI27648.2132

Ma, J., Liu, L., Che, G., Yu, N., Dai, F., & You, Z. (2010). The M1 form of tumor-associated macrophages in non-small cell lung cancer is positively associated with survival time. BMC Cancer, 10, 112. http://doi.org/10.1186/1471-2407-10-112

Mandal, P., Pratt, B. T., Barnes, M., McMullen, M. R., & Nagy, L. E. (2011).

TABLE OF REFERENCES B

Molecular mechanism for adiponectin-dependent M2 macrophage polarization: link between the metabolic and innate immune activity of full-length adiponectin. The Journal of Biological Chemistry, 286(15), 13460-9. http://doi.org/10.1074/jbc.M110.204644

Mantovani, A., Allavena, P., Sica, A., & Balkwill, F. (2008). Cancer-related inflammation. Nature, 454(7203), 436-44. http://doi.org/10.1038/nature07205

Mantovani, A., Biswas, S. K., Galdiero, M. R., Sica, A., & Locati, M. (2013). Macrophage plasticity and polarization in tissue repair and remodelling. The Journal of Pathology, 229(2), 176-85. http://doi.org/10.1002/path.4133

Mantovani, A., Sozzani, S., Locati, M., Allavena, P., & Sica, A. (2002). Macrophage polarization: tumor-associated macrophages as a paradigm for polarized M2 mononuclear phagocytes. Trends in Immunology, 23(11), 549-55. Retrieved from http://www.ncbi.nlm.nih.gov/pubmed/12401408

Michel, O., & Nagy, A. (1997). Dose-response relationship to inhaled endotoxin in normal subjects. American Journal of Respiratory and Critical Care Medicine, 156(4 Pt 1), 1157-64. Retrieved from http://www.atsjournals.org/doi/abs/10.1164/ajrccm.156.4.97-02002

Mills, C. D., Shearer, J., Evans, R., & Caldwell, M. D. (1992). Macrophage arginine metabolism and the inhibition or stimulation of cancer. Journal of Immunology (Baltimore, Md.: 1950), 149(8), 2709-14. Retrieved from http://www.ncbi.nlm.nih.gov/pubmed/1401910

Murray, P. J., Allen, J. E., Biswas, S. K., Fisher, E. A., Gilroy, D. W., Goerdt, S., . . . Wynn, T. A. (2014). Macrophage Activation and Polarization: Nomenclature and Experimental Guidelines. Immunity, 41(1), 14-20. http://doi.org/10.1016/j.immuni.2014.06.008

Ohri, C. M., Shikotra, A., Green, R. H., Waller, D. a, & Bradding, P. (2009). Macrophages within NSCLC tumour islets are predominantly of a cytotoxic M1 phenotype associated with extended survival. The European Respiratory Journal, 33(1), 118-26. http://doi.org/10.1183/09031936.00065708

Porta, C., Rimoldi, M., Raes, G., Brys, L., Ghezzi, P., Di Liberto, D., . . . Sica, A. (2009). Tolerance and M2 (alternative) macrophage polarization are related processes orchestrated by p50 nuclear factor kappaB. Proceedings of the National Academy of Sciences of the United States of America, 106(35), 14978-83. http://doi.org/10.1073/pnas.0809784106

Qin, X.-Q., Runkel, L., Deck, C., DeDios, C., & Barsoum, J. (1997). Interferon-beta induces S phase accumulation selectively in human transformed cells. Journal of Interferon & Cytokine Research, 17(6), 355-367. http://doi.org/10.1089/jir.1997.17.355

Rogers, T. L., & Nolen, I. (2011). Tumour macrophages as potential targets of bisphosphonates. Journal of Translational Medicine, 9(1), 177. http://doi.org/10.1186/1479-5876-9-177

Saccani, A., Schioppa, T., Porta, C., Biswas, S. K., Nebuloni, M., Vago, L., . . . Sica, A. (2006). p50 nuclear factor-kappaB overexpression in tumor-associated macrophages inhibits M1 inflammatory responses and antitumor resistance. Cancer Research, 66(23), 11432-40. http://doi.org/10.1158/0008-5472.CAN-06-1867

Sanford, D. E., Belt, B. A., Panni, R. Z., Mayer, A., Deshpande, A. D., Carpenter, D., . . . Linehan, D. C. (2013). Inflammatory monocyte mobilization decreases patient survival in pancreatic cancer: a role for targeting the CCL2/CCR2 axis. Clinical Cancer Research: An Official Journal of the American Association for Cancer Research, 19(13), 3404-15. http://doi.org/10.1158/1078-0432.CCR-13-0525

Schmall, A., Al-Tamari, H. M., Herold, S., Kampschulte, M., Weigert, A., Wietelmann, A., . . . Savai, R. (2014). Macrophage and Cancer Cell Crosstalk via CCR2 and CX3CR1 is a Fundamental Mechanism Driving Lung Cancer. American Journal of Respiratory and Critical Care Medicine. http://doi.org/10.1164/rccm.201406-1137OC Shaw, R. J. (2006). Glucose metabolism and cancer. Current Opinion in Cell Biology, 18(6), 598-608. http://doi.org/10.1016/j.ceb.2006.10.005

Shu, C. J., Guo, S., Kim, Y. J., Shelly, S. M., Nijagal, A., Ray, P., . . . Witte, O. N. (2005). Visualization of a primary anti-tumor immune response by positron emission tomography. Proceedings of the National Academy of Sciences of the United States of America, 102(48), 17412-7. http://doi.org/10.1073/pnas.0508698102

Sica, A., & Mantovani, A. (2012). Macrophage plasticity and polarization: in vivo veritas. The Journal of Clinical Investigation, 122(3), 787-796. http://doi.org/10.1172/JCI59643DS1

Simons, J. W., Carducci, M. a, Mikhak, B., Lim, M., Biedrzycki, B., Borellini, F., . . . Nelson, W. G. (2006). Phase I/II trial of an allogeneic cellular immunotherapy in hormone-naïve prostate cancer. Clinical Cancer Research, 12(11 Pt 1), 3394-401. http://doi.org/10.1158/1078-0432.CCR-06-0145

Simpson, K. D., Templeton, D. J., & Cross, J. V. (2012). Macrophage Migration Inhibitory Factor Promotes Tumor Growth and Metastasis by Inducing Myeloid-Derived Suppressor Cells in the Tumor Microenvironment. The Journal of Immunology. http://doi.org/10.4049/jimmunol.1201161

Sinha, P., Clements, V. K., & Ostrand-Rosenberg, S. (2005). Reduction of myeloid-derived suppressor cells and induction of M1 macrophages facilitate the rejection of established metastatic disease. Journal of Immunology,

TABLE OF REFERENCES B

174(2), 636-45. Retrieved from
http://www.ncbi.nlm.nih.gov/pubmed/15634881
Smith, H. O., Stephens, N. D., Qualls, C. R., Fligelman, T., Wang, T., Lin, C.-Y., . . .
Pollard, J. W. (2013). The clinical significance of inflammatory cytokines
in primary cell culture in endometrial carcinoma. Molecular Oncology, 7(1),
41-54. http://doi.org/10.1016/j.molonc.2012.07.002
Squadrito, M. L., Etzrodt, M., De Palma, M., & Pittet, M. J. (2013). MicroRNA-
mediated control of macrophages and its implications for cancer. Trends in
Immunology, 34(7), 350-9. http://doi.org/10.1016/j.it.2013.02.003
Steidl, C., Lee, T., & Shah, S. (2010a). Tumor-associated macrophages and
survival in classic Hodgkin's lymphoma. The New England Journal of
Medicine, 875-885. Retrieved from
http://www.nejm.org/doi/full/10.1056/NEJMoa0905680
Steidl, C., Lee, T., & Shah, S. (2010b). Tumor-associated macrophages and
survival in classic Hodgkin's lymphoma. The New England Journal of
Medicine, 362(10), 875-885. Retrieved from
http://www.nejm.org/doi/full/10.1056/NEJMoa0905680
Urban, J. L., Shepard, H. M., Rothstein, J. L., Sugarman, B. J., & Schreiber, H.
(1986). Tumor necrosis factor: a potent effector molecule for tumor cell
killing by activated macrophages. Proceedings of the National Academy of
Sciences of the United States of America, 83(14), 5233-7. Retrieved from
http://www.pubmedcentral.nih.gov/articlerender.fcgi?artid=323925&tool=pmcentrez&rendertype=abstract
Van Ginderachter, J. A., Movahedi, K., Hassanzadeh Ghassabeh, G.,
Meerschaut, S., Beschin, A., Raes, G., & De Baetselier, P. (2006). Classical
and alternative activation of mononuclear phagocytes: Picking the best of both
worlds for tumor promotion. Immunobiology, 211(6), 487-501. Retrieved from
http://www.sciencedirect.com/science/article/pii/S0171298506000829
Wang, Y.-C., He, F., Feng, F., Liu, X.-W., Dong, G.-Y., Qin, H.-Y., . . . Han, H.
(2010). Notch signaling determines the M1 versus M2 polarization of
macrophages in antitumor immune responses. Cancer Research, 70(12),
4840-9. http://doi.org/10.1158/0008-5472.CAN-10-0269
Wei, Y., Nazari-Jahantigh, M., Chan, L., Zhu, M., Heyll, K., Corbalán-Campos, J., . . .
Schober, A. (2013). The microRNA-342-5p fosters inflammatory
macrophage activation through an Akt1- and microRNA-155-dependent
pathway during atherosclerosis. Circulation, 127(15), 1609-19.
http://doi.org/10.1161/CIRCULATIONAHA.112.000736
West, R. B., Rubin, B. P., Miller, M. A., Subramanian, S., Kaygusuz, G.,
Montgomery, K., . . . van de Rijn, M. (2006). A landscape effect in tenosynovial
giant-cell tumor from activation of CSF1 expression by a translocation in a
minority of tumor cells. Proceedings of the National Academy of Sciences of
the United States of America, 103(3), 690-5.
http://doi.org/10.1073/pnas.0507321103
Wolf, A., Agnihotri, S., Micallef, J., Mukherjee, J., Sabha, N., Cairns, R., . . .
Guha, A. (2011). Hexokinase 2 is a key mediator of aerobic glycolysis and
promotes tumor growth in human glioblastoma multiforme. The Journal of
Experimental Medicine, 208(2), 313-26. http://doi.org/10.1084/jem.20101470
Wong, S.-C., Puaux, A.-L., Chittezhath, M., Shalova, I., Kajiji, T. S., Wang, X., . . .
Biswas, S. K. (2010). Macrophage polarization to a unique phenotype
driven by B cells. European Journal of Immunology, 40(8), 2296-307.
http://doi.org/10.1002/eji.200940288
Zeisberger, S. M., Odermatt, B., Marty, C., Zehnder-Fjällman, a H. M.,
Ballmer-Hofer, K., & Schwendener, R. a. (2006). Clodronate-liposome-
mediated depletion of tumour-associated macrophages: a new and highly
effective antiangiogenic therapy approach. British Journal of Cancer, 95(3),
272-81. http://doi.org/10.1038/sj.bjc.6603240
Zhang, F., Lu, W., & Dong, Z. (2002). Tumor-infiltrating macrophages are
involved in suppressing growth and metastasis of human prostate cancer cells
by INF-β gene therapy in nude mice. Clinical Cancer Research, 2942-2951.
Retrieved from http://clincancerres.aacrjournals.org/content/8/9/2942.short

The invention claimed is:

1. A method for administering cells to a tumor in a subject, the method comprising:
    administering to the subject human monocyte cells;
    wherein the monocyte cells comprise a gene encoding a chimeric antigen receptor (CAR);
    wherein the CAR comprises a fusion of an antigen binding antibody fragment and a TLR-4 cytoplasmic signaling domain, the cytoplasmic signaling domain polarizing the cells to M1 phenotype macrophages upon binding of the antibody fragment to its antigen.

2. The method according to claim 1, wherein the antibody fragment is a single chain variable fragment (scFv).

3. The method according to claim 1, wherein the antigen is HGPRT.

4. The method according to claim 2, wherein the scFv is derived from a monoclonal antibody specific for an antigen expressed by cells of a cancer.

5. The method according to claim 1, wherein the antigen is present on cells of a cancer.

6. The method according to claim 4, wherein the monoclonal antibody is a human or mouse monoclonal antibody.

7. The method according to claim 1, wherein the macrophages are stimulated by a co-stimulatory molecule.

8. The method according to claim 7, wherein the co-stimulatory molecule is MD2 or CD14.

9. A method for administering cells to a tumor in a subject, the method comprising:
- administering to the subject human monocyte cells;
- wherein the monocyte cells comprise a gene encoding a chimeric antigen receptor (CAR);
- wherein the gene encoding the CAR comprises a macrophage specific promoter;
- wherein the CAR comprises a fusion of an antigen binding antibody fragment and a TLR-4 cytoplasmic signaling domain, the cytoplasmic signaling domain polarizing the cells to M1 phenotype macrophages upon binding of the antibody fragment to its antigen; and
- wherein the antigen is TK1.

10. The method according to claim 1, wherein the antigen is a salvage pathway enzyme.

11. The method according to claim 10, wherein the salvage pathway enzymes is selected from the group consisting of TK1, HGPRT, DCK, and APRT.

12. The method according to claim 1, wherein the gene encoding the CAR comprises a macrophage specific promoter.

* * * * *